US007638678B2

(12) United States Patent
Hoyer et al.

(10) Patent No.: US 7,638,678 B2
(45) Date of Patent: Dec. 29, 2009

(54) ANIMAL MODEL FOR PERIMENOPAUSE AND MENOPAUSE AND METHODS OF INDUCING OVARIAN FAILURE

(75) Inventors: Patricia B. Hoyer, Tucson, AZ (US); Loretta P. Mayer, Flagstaff, AZ (US)

(73) Assignee: The Arizona Board of Regents, Tucson, AZ (US)

( * ) Notice: Subject to any disclaimer, the term of this patent is extended or adjusted under 35 U.S.C. 154(b) by 646 days.

(21) Appl. No.: 10/650,799

(22) Filed: Aug. 29, 2003

(65) Prior Publication Data

US 2004/0073962 A1 Apr. 15, 2004

Related U.S. Application Data

(60) Provisional application No. 60/406,671, filed on Aug. 29, 2002.

(51) Int. Cl.
*G01N 33/00* (2006.01)
*A01K 67/00* (2006.01)
*A01K 67/033* (2006.01)
*A01K 67/027* (2006.01)
(52) U.S. Cl. .................................. 800/9; 800/3; 800/14
(58) Field of Classification Search ..................... 800/9, 800/3, 14
See application file for complete search history.

(56) References Cited

U.S. PATENT DOCUMENTS

| | | | |
|---|---|---|---|
| 6,107,540 | A | 8/2000 | Sawyer et al. |
| 6,583,334 | B1 | 6/2003 | Haslam |

OTHER PUBLICATIONS

Acarturk, F and Robinson, Jr. Vaginal permeability and enzymatic activity studies in normal and ovariectomized rabbits, Pharmaceutical Research, 13:779-783, 1996.*
Abel, TW et al., The effects of hormone replacement therapy on hypothalmic neuropeptide gene expression in a primate model of menopause. Jour Clin Endocrin Metab, 84:2111-2118, 1999.*
Osei-Hiyaman, D et al, 1998, Amer Jour Epidemiology, 148:1055-1061.*
Amant, C et al, 2001, Criculation, 104:2576-2581.*
Mulholland, SG, 1982, Journal of Urology, 127:1010-1013.*
B. J. Smith, et al., Reproductive Toxicology, vol. 5, No. 4, pp. 379-383, "Comparison of Random and Serial Sections in Assessment of Ovarian Toxicity", 1991.
Written Opinion, Mar. 30. 2005.
Loretta P. Mayer, et al., "The foll cle-Deplete Mouse Ovary Produces Androgen", Biology of Reproduction, vol. 71, No. 1, XP-002368701, Jul. 2004, pp. 130-138.
Miriam J.J. de Kleijn et al.; "Endogenous Estrogen Exposure and Cardivascular Mortality Risk in Postmenopausal Women"; American Journal of Epidemiology, vol. 155, No. 4, pp. 339-345; 2002.
Caren G. Solomon et al.: "Menstrual Cycle Irregularity and Risk for Future Cardiovascular Disease"; The Journal of Clinical Endocrinology & Metabolism, 87(5), pp. 2013-2017; 2002.

Frank B. Hu, MD et al.; "Age at Natural Menopause and Risk of Cardiovascular Disease"; Arch Intern Med/vol. 159, pp. 1061-1066; May 24, 1999.
Francine Grodstein et al; "A Prospective, Observational Study of Postmenopausal Hormone Therapy and Primary Prvention of Cardiovascular Disease"; Annals of Internal Medicine, vol. 133, No. 12; pp. 933-941; Dec. 19, 2000.
Francine Grodstein et al; "Postmenopausal Hormone Use and Secondary Prevention of Coronary Events in the Nurses' Health Study"; Annals of Internal Medicine; vol. 135, No. 1, pp. 1-8; Jul. 3, 2001.
Frank B. Hu, MD et al.; "Postmenopausal Hormone Therapy and the Risk of Cardiovascular Disease: The Epidemiologic Evidence"; The American Journal of Cardiology; vol. 90(1A), pp. 26F-29F; Jul. 3, 2002.
NIH: Postmenopausal Hormone Therapy Information; http://www.nih.gov/PHTindex.htm; 4pp., Jul. 26, 2003.
Karin H. Humphries et al; "Risks and benefits of hormone replacement therapy: The evidence speaks"; Canadian Medical Association, 168(8), pp. 1001-1010; Apr. 15, 2003.
Gail A. Laughlin et al; "Hysterectomy, Oophorectomy, and Endogenous Sex Hormone Levels in Older Women: The Rancho Bernardo Study"; The Journal of Clinical Endocrinology & Metabolism; vol. 85, No. 2, pp. 645-651; 2000.
Manuel Neves-e-Castro et al; "Results from WHI and HERS II—Implications for Women and the prescriber of HRT"; Maturitas 42 (2002) 255-258.
Bjarne K. Jacobsen et al' "Age at Natural Menopause and All-Cause Mortality: A 37-Year Follow-up of 19/731 Norwegian Women"; American Journal of Epidemiology, vol. 157, No. 10, pp. 923-929; 2003.
Sally A. Shumaker, Ph.D. et al; "Estrogen Plus Progestin and the Incidence of Dementia and Mild Cognitive Impairment in Postmenopausal Women The Women's Health Initiative Memory Study: A Randomized Controlled Trial"; JAMA, vol. 289, No. 20 (Reprinted), pp. 2651-2662; May 28, 2003.
Peter P. Zandi, Ph.D. et al.; "Hormone Replacement Therapy and Incidence of Alzheimer Disease in Older Women The Cache County Study"; JAMA, vol. 288, No. 17, pp. 2123-2129; Nov. 6, 2002.
Susan M. Fontaine et al; "Stereochemical Aspects of Vinylcyclohene Bioactivation in Rodent Hepatic Microsomes and Purified Human Cytochrome P450 Enzyme Systems"; DMD, vol. 29, No. 2, pp. 179-184; 2001.
S.M. Borman et al; "Ovotoxicity in Female Fischer Rats and B6 Mice Induced by Low-Dose Exposure to Three Polycyclic Aromatic Hydrocarbons: Comparison through Calculation of an Ovotoxic Index"; Toxicology and Applied Pharmacolocy, vol. 167, pp. 191-198; 2000.
Patricia B Hoyer et al; "Ovarian Toxicity of 4-Vinylcyclohexene Diepoxide: A Mechanistic Model"; Toxicologic Pathology, vol. 29, No. 1, pp. 91-99; 2001.

(Continued)

*Primary Examiner*—Valarie Bertoglio
(74) *Attorney, Agent, or Firm*—Oblon, Spivak, McClelland, Maier & Neustadt, L.L.P.

(57) ABSTRACT

The present invention relates to an animal model for human perimenopause and menopause. Also provided by the present invention are methods of making the animal model and methods of screening using the model. Also provided are methods of inducing ovarian failure in animals such as pets and wildlife.

36 Claims, 8 Drawing Sheets

OTHER PUBLICATIONS

Patricia B. Hoyer et al; "Assessment of Follicle Desruction in Chemical-Induced Ovarian Toxicity"; Annu. Rev. Pharmacol. Toxicol., vol. 36, pp. 307-331; 1996.

Loretta P. Mayer et al; "Long-term effects of ovarian follicular depletion in rats by 4-vinylcyclohexene diepoxide"; Reproductive Toxicology, vol. 16, pp. 775-781; 2002.

Stephen B. Hooser et al; "Long-Term Ovarian and Gonadotropin Changes in Mice Exposed to 4-Vinylcyclohexene"; Reproductive Toxicology, vol. 8, No. 4, pp. 315-323; 1994.

Bill J. Smith et al; "The Role of Epoxidation in 4-Vinylcyclohexene-Induced Ovarian Toxicity"; Toxicology and Applied Pharmacology, vol. 105, pp. 372-381; 1990.

L.N. Springer et al; "Involvement of Apoptosis in 4-Vinylcyclohexene Diepoxide-Induced Ovotoxicity in Rats[1]" Toxicology and Applied Pharmacology, vol. 139, pp. 394-401; 1996.

P.J. Devine et al; "Ultrastructural Evaluation of Oocytes During Atresia in Rat Ovarian Follicles[1]"; Biology of Reproduction, vol. 63, pp. 1245-1252; 2000.

Xiaming Hu et al; "Expression and Redistribution of Cellular Bad, Bax and Bcl-$X_L$ Protein Is Associated with VCD-Induced Ovotoxicity in Rats[1]" Biology of Reproduction, vol. 65, pp. 1489-1495; 2001.

Xiaoming Hu et al; "Apoptosis Induced in Rats by 4-Vinylcyclohexene Diepoxide is Associated with Activation of Caspase Cascades[1]"; Biology of Reporduction, vol. 65, pp. 87-93; 2001.

Xiaoming Hu et al; "Activation of Mitogen-Activated Protein Kinases and AP-1 Transcription Factor in Ovotoxicity Induced by 4-Vinylcyclohexene Diepoxide in Rats[1]"; Biology of Reproduction, vol. 67, pp. 718-724; 2002.

S.M. Borman et al; "Single Dose of the Ovotoxicant 4-Vinylcyclohexene Diepoxide Is Protective in Rat Primary Ovarian Follicles"; Toxicology and Applied Pharmacology, vol. 158, pp. 244-252; 1999.

Kary E. Tohmpson et al; "17β-Estradiol Affords Protection against 4-Vinylcyclohexene Diepoxide-Induced Ovarian Follicle Loss in Fischer-344 Rats"; Endocrinology, 143(3), pp. 1058-1065; Mar. 2002.

Lori Mosca, MD et al; "Cardiovascular Disease in Women A Statemtn for Healthcare Professionals From the American Heart Association"; Circulation, vol. 96, No. 7, pp. 2468-2482; Oct. 7, 1997.

Suzanne Oparil; Supplement to Hypertension; Arthur C. Corcoran Memorial Lecture; "Hormones and Vasoprotection"; Journal of the American Heart Association, vol. 33, No. 1, Part II; Jan. 1999.

Stephen Hulley, MD et al; "Randomized Trial of Estrogen Plus Progestin for Secondary Prevention of Coronary Heart Disease in Postmenopausal Women"; JAMA, vol. 280, No. 7, pp. 605-613; Aug. 19, 1998.

Dr. Anderson et al; "Risks and Benefits of Estrogen Plus Progestin in Healthy Postmenopausal Women"; JAMA, vol. 288, No. 3, pp. 321-333; Jul. 17, 2002.

David W. Purdie; "Consequences of long-term hormone replacement therapy"; British Medical Bulletin, vol. 56, No. 3, pp. 809-823; 2000.

Carmen Rodriguez, MD, MPH et al; "Estrogen Replacement Therapy and Ovarian Cancer Mortality in a Large Prospective Study of US Women"; JAMA, vol. 285, No. 11, pp. 1460-1465; Mar. 21, 2001.

Francis L. Bellino, Ph.D.; "Nonprimate Animal Models of Menopause: Workshop Report"; Menopause: The Journal of the North American Menopause Society, vol. 7, No. 1, pp. 14-24; 2000.

Howard L. Judd, MD; "Hormonal Dynamics Associated with the Menopause"; Clinical Obsterics and Gynecology, vol. 19, No. 4, pp. 775-788; Dec. 1976.

Jodi A. Flaws et al; "Destruction of Preantral Follicles in Adult Rats By 4-Vinylcyclohexene Diepoxide"; Reproductive Toxicology, vol. 8, No. 6, pp. 500-514; 1994.

Shao-Wen Kao et al; "Early Effects of Ovotoxicity Induced By 4-Vinylcyclohexene Diepoxide in Rats and Mice"; Reproductive Toxicology, vol. 13, No. 1, pp. 67-75; 1999.

Gregory F. Erickson; Menopause Biology and Pathobiology; "Ovarian Anatomy and Physiology"; Chapter 2, pp. 13-31; 2000.

Cheryl A. Dyer, Ph.D., Alzeimer's Association, KRS: Application form for Individual Research Project, Project Title: Apo E isoform effect on perimenopausal ovarian steroids and risk for AD, 2003.

Patricia B. Hoyer, Research Plan, Grant Application, PHS 398/2590, pp. 17-47, 2003.

Loretta P. Mayer, Grant Proposal, AIM III, p. 25, reviewed Oct. 19, 2007.

Loretta P. Mayer et al., Preprint of an article entitled The Follicle-Depleted Mouse Ovary Produces Androgen, reviewed Oct. 19, 2007.

Loretta P. Mayer et al., Jul. 2001 Presentation to the Ottowa Society for Study of Reproduction, Long-Term Effects of Ovotoxicity in Rats Exposed to 4-Vinylcyclohexene Diepoxide.

Loretta P. Mayer et al., Abstract and Poster Presentation, "An ovary-intact mouse model that mimics peri-menopause in women", Published after Sep. 20, 2002.

L.P. Mayer et al., Abstract and Poster Presentation at the Endocrinology annual meeting in San Francisco, "Development of an Ovary-Intact Murine Model for the Study of Menopause-related Pathologies", Jun. 2002.

GM Buss et al., Abstract and Poster Presentation, Presented at the Moutain West Society for Toxicology, Sep. 20, 2001, "Steroidogenic Responsiveness of 4-Vinylcyclohexene Diepoxide (VCD-Induced Follicle-Deplete Murine Ovaries to Gonadotropin Stimulation in Vitro".

Hoyer and Mayer, "Background and Significance," Unpublished Summary, Mar. 2002, pp. 1-7.

Loretta P. Mayer et al., Poster Presentation at the Atherosclerosis, Thrombosis and Vascular Biology Meeting of the American Heart Association, Spring (Mar.?) 2002.

In House Talk done by Oct. 30, 2001, entitled Mouseopause: A model whose time has come.

* cited by examiner

B VCD

C Control

ANIMAL MODEL FOR PERIMENOPAUSE AND MENOPAUSE AND METHODS OF INDUCING OVARIAN FAILURE

CONTINUING APPLICATION DATA

This application claims the benefit of the filing date of U.S. provisional application Ser. No. 60/406,671, filed on Aug. 29, 2002, the contents of which are incorporated herein by reference.

STATEMENT REGARDING FEDERALLY SPONSORED RESEARCH

This invention was supported by NIH via grant numbers RO1-ES9246, RO1-ES8979, and RO1-AG021948. The government may have certain rights to this technology.

BACKGROUND OF THE INVENTION

1. Field of the Invention

The present invention relates to an animal model for human perimenopause and menopause. Also provided by the present invention are methods of making the animal model and methods of screening and using the model. Also provided are methods of inducing ovarian failure in animals such as pets and wildlife.

2. Description of the Background

The average age of menopause in women in the U.S. is 51 years. Demographic studies on the age of menopause have shown that it has increased from about 45 years in 1850, to approximately 51 in 1995. At the same time, however, the life expectancy of women has increased from 45 in 1850 to approximately 82 in 1998. As a result, because the life span in women has increased, almost 30% of a woman's lifetime will be postmenopausal (1). The consequence of this shift is that many age-related diseases are increasing in incidence and need to be investigated in relevant animal models to understand the effect of menopause on disease risk, presentation and progression. Many disorders such as Alzheimer's disease have an increased incidence in females of a relatively late onset (approximately 80 years of age). Obviously, in the future, the increase in life expectancy will impact the incidence of many age-related diseases and require aggressive intervention during the postmenopausal years.

Many health risks are known to be associated with menopause. There is a strong direct link between menopause and an increase in cardiovascular disease which is the leading cause of death in women over the age of 50 (2). A number of observational studies have, provided evidence that hormone replacement therapy (HRT) reduces the risk of cardiovascular disease by about one-half (3). However, the HERS study recently reported that HRT in post menopausal women did not prevent recurrent myocardial infarction (4). Recently, the Womens Health Initiative study conducted by the NIH reported a slight increase in cardiovascular disease-associated conditions in women taking HRT (5). Furthermore, there is a significant debate over the advantages and disadvantages of using HRT in postmenopausal women relative to a potential increase in both breast and ovarian cancer risks (5, 6, 7). Clearly, studies utilizing a relevant animal model would contribute greatly to resolving these issues. Interestingly, although controversial, it has been suggested that there are benefits rather than risks associated with the estrogens in birth-control pill usage in premenopausal women (7). These seemingly disparate effects of estrogen treatment will best be resolved in the laboratory.

Menopause is the cessation of ovarian cyclicity resulting from the depletion of ovarian follicles by a natural process of atrition, known as atresia (8). Follicular maturation in the ovary is a dynamic series of events in which primordial follicles provide a finite pool from which preovulatory follicles are selected for development and ovulation, or are eliminated by atresia. The primordial follicle, the most immature stage of development, is formed in the ovary during fetal development. Because the oocyte is arrested in meiosis, this pool is non-regenerating after birth. In an on-going process, after puberty, follicles continually progress from the primordial to ovulatory stages. However, the vast majority do not develop to ovulation, but undergo cell death by atresia. As a result, the pool of primordial follicles gradually becomes depleted and ultimately, ovarian failure (menopause) ensues (8). As the pool of primordial follicles is depleted, this compromises the numbers of developing preovulatory follicles. Eventually, the reduction in pre-ovulatory follicles significantly alters ovarian steroid hormone production as a woman approaches menopause (perimenopause), resulting in a sharp decrease in circulating 17β-estradiol and a concomitant rise in the gonadotropins follicle stimulating hormone (FSH) and luteinizing hormone (LH), due to loss of negative feedback from the ovary to the pituitary. Thus, following menopause, hormonal cyclicity ceases within the ovary and it secretes primarily androgens in a hypergonadotropic environment (8). Because 17β-estradiol is assumed to afford protection in premenopausal women against health risks, such as cardiovascular disease, skeletal problems, and brain dysfunction, the loss of 17β-estradiol in menopause is thought to contribute to most menopause-associated disorders.

In researching menopause, a limited amount of mechanistic information can be obtained from studies in middle-aged women. Therefore, the elucidation of underlying cellular and molecular mechanisms that accompany menopause-associated disorders requires the use of appropriate animal models in controlled experimental conditions. Although nonhuman primates most closely resemble humans, there are disadvantages in using them in the study of menopause. These include limitations on the number of animals, costly acquisition and housing expenses, and lengthy life spans, with reproductive senescence occurring late in life (9). Rodent models, on the other hand, are inexpensive and reproductive senescence can be caused and studied within a relatively short time frame. Previous rodent studies have attempted to model menopause by ovariectomy. While this approach mimics the loss of 17β-estradiol seen in menopause, it lacks consideration of the physiological contributions of the postmenopausal ovary. It is possible that the postmenopausal ovary impacts the effects of the changing hormonal and gonadotropin milieu via secretion of bioregulatory factors. In postmenopausal women who have had their ovaries removed, a 50% reduction in testosterone has been observed, indicating that the senescent ovary is secreting androgens that have the potential to impact postmenopausal health risks (10). However, because there has not heretofore been an adequate animal model of the postmenopausal ovary, this issue has not been directly investigated. In surgical experiments conducted in mice, aged ovaries were transplanted into young ovex recipients. Plasma FSH levels were significantly increased compared to controls, indicating that the aged ovary plays a role in reproductive failure by impacting the hypothalamic-pituitary-ovarian axis, perhaps by as yet-unknown bioregulatory factors as well as loss of negative feedback due to a reduction in 17β-estradiol. Collectively, the lack of information about the follicle-depleted ovary supports the need for investigations into its function in vivo as well as in vitro to understand the effects on age-related diseases associated with menopause.

The occupational chemical VCD, the diepoxide metabolite of 4-vinylcyclohexene (VCH), causes selective loss of small preantral follicles in the ovaries of mice and rats (11-13). Compared to vehicle controls, VCD dosing of rats and mice for 12 days caused a significant reduction in the number of primordial and primary follicles (12). However, following 30 days of dosing there was also a significant reduction in the numbers of secondary follicles (11, 13) which was explained as a reduction in the pool of primordial follicles from which secondary follicles could be recruited at that time to develop into large antral follicles that produce 17β-estradiol. The targeting of primordial and primary follicles by VCD appears to be follicle stage-specific because no direct effects have been observed or measured in larger (secondary to antral) follicles, or other non-ovarian tissues as determined by necropsy, histopathology, plasma lipid profiles, and liver enzyme activity. Using a combination of molecular and cellular approaches in our studies in rats we have collected evidence that VCD-induced follicle loss is by acceleration of the normal rate of atresia. These studies have also demonstrated that alterations in apoptosis-associated intracellular pathways activated by VCD dosing are specific for small preantral follicles, as compared with large preantral follicles or liver. Atresia in the rodent ovary occurs via apoptosis, or programmed cell death, and is a normal process without necrosis-induced responses such as inflammation. Evidence of VCD-induced impending follicle loss was observed as an increase in numbers of unhealthy follicles in the treated group. The unhealthy appearance in VCD-treated ovaries is morphologically and ultrastructurally similar to unhealthy follicles undergoing natural atresia in controls (14-16). At the molecular level, VCD-accelerated atresia in small preantral follicles was identified because intracellular events associated with apoptosis were measured selectively in the targeted follicular population. These events include: A) increased Bax/BclxL ratio (17), B) increased expression of Bad, C) leakage of cytochrome c from mitochondria into the cytosol (18), D) increased caspase-3 activity (18), E) activation of the JNK and p38 branch of the MAPK signaling pathway (19), F) retardation of natural atresia and bax expression (relative to controls) in small follicles following a single dose of VCD (20) and G) estrogen receptor-mediated protection from VCD-induced follicle loss (21). Collectively, these data support at a molecular level that VCD causes follicle loss by enhancing events associated with the normal process of atresia. These molecular events are specific for the small preantral follicles known to be physiologically targeted by VCD.

Follicle loss resulting from repeated dosing of F344 rats with VCD has been well characterized (11-21). The conclusion from characterization performed in preliminary studies is that VCD causes the selective loss of primordial and primary follicles by accelerating the natural process of atresia via apoptosis. In long term studies in B6C3F$_1$ mice (22) and F344 rats (15) that were dosed with the parent compound, 4-vinylcyclohexene (VCH, mice) or the ovotoxic form (VCD, rats), premature ovarian failure occurred within a year. However, the time it takes from dosing of the animals until premature ovarian failure occurs is too long in order to use animals prepared in such a manner as a model for menopause.

The development of an animal model that mimics the onset of menopause is critical to enhance an understanding of the role of menopause in many age-related diseases. By using VCD to chemically accelerate the normal process of atresia selectively in primordial and primary follicles, it would be possible to more accurately approximate the physiological events that occur during the progression from ovarian function through impending ovarian failure (perimenopause), to the eventual disease risks that result after menopause. Therefore, such a model would be powerful in scope because a wide variety of physiological and molecular endpoints can be designed for understanding the complexities of health risks that accompany menopause in women.

SUMMARY OF THE INVENTION

It is an object of the present invention to provide a non-human female animal suitable as a model of human perimenopause and/or menopause.

It is another object of the invention to provide methods of making the animal model.

It is another object of the invention to provide a method of screening an agent for its effect on a non-human female animal suitable as a model of human perimenopause and/or menopause. In one specific aspect of this embodiment, such a method provides for screening of agents which may be useful for preventing or treating a condition associated with or caused by perimenopause and/or menopause.

It is another object of the present invention to provide methods of inducing ovarian failure in mammalian female animals.

The objects of the present invention, and others, may be accomplished with a mammalian non-human female animal having at least a partial depletion of ovarian primordial follicles and at least one characteristic of perimenopause and/or menopause induced by administration of at least one compound selected from the group consisting of 4-vinylcyclohexene diepoxide (VCD), 4-vinylcyclohexene (VCH), 4-vinylcyclohexene-1,2-epoxide (VCH-1,2-epoxide), and 4-vinylcyclohexene-7,8-epoxide (VCH-7,8-epoxide).

The objects of the present invention may also be accomplished with a method of making the animal model described above by administering to the animal an effective amount at least one compound selected from the group consisting of 4-vinylcyclohexene diepoxide, 4-vinylcyclohexene, 4-vinylcyclohexene-1,2-epoxide, and 4-vinylcyclohexene-7,8-epoxide to cause at least a partial depletion of ovarian primordial follicles and at least one characteristic of perimenopause or menopause.

The objects of the present invention may also be accomplished with a method of screening an agent, comprising:
administering an agent to the animal described above; and
evaluating the effect of the agent on the animal.

The objects of the present invention may also be accomplished with a method of inducing ovarian failure in a non-human mammalian female animal other than a mouse or a rat, comprising administering to the animal an effective amount of at least one compound selected from the group consisting of 4-vinylcyclohexene diepoxide, 4-vinylcyclohexene, 4-vinylcyclohexene-1,2-epoxide, and 4-vinylcyclohexene-7,8-epoxide.

The objects of the present invention may also be accomplished with a method of sterilizing a mammalian non-human female animal other than a mouse or a rat, comprising administering to the animal an effective amount of at least one compound selected from the group consisting of 4-vinylcyclohexene diepoxide, 4-vinylcyclohexene, 4-vinylcyclohexene-1,2-epoxide, and 4-vinylcyclohexene-7,8-epoxide.

The objects of the present invention may also be accomplished with a method of controlling the size of a non-human mammalian animal population, comprising administering an effective amount of at least one compound selected from the group consisting of 4-vinylcyclohexene diepoxide, 4-vinylcyclohexene, 4-vinylcyclohexene-1,2-epoxide, and 4-vinyl-cyclohexene-7,8-epoxide to the animal population sufficient to cause at least partial ovarian failure in at least a portion of the female members of the animal population.

The objects of the present invention may also be accomplished with a solid composition suitable for oral administration, comprising at least one compound selected from the group consisting of 4-vinylcyclohexene diepoxide, 4-vinyl-cyclohexene, 4-vinylcyclohexene-1,2-epoxide, and 4-vinyl-cyclohexene-7,8-epoxide and a solid excipient.

The objects of the invention may also be accomplished with a composition suitable for dermal or subcutaneous delivery to an animal, comprising at least one compound selected from the group consisting of 4-vinylcyclohexene diepoxide, 4-vinylcyclohexene, 4-vinylcyclohexene-1,2-epoxide, and 4-vinylcyclohexene-7,8-epoxide in a dermal or subcutaneous delivery device.

A more complete appreciation of the invention and many of the attendant advantages thereof will be readily obtained as the same becomes better understood by reference to the following figures and detailed description.

DETAILED DESCRIPTION OF THE INVENTION

Figure 1:
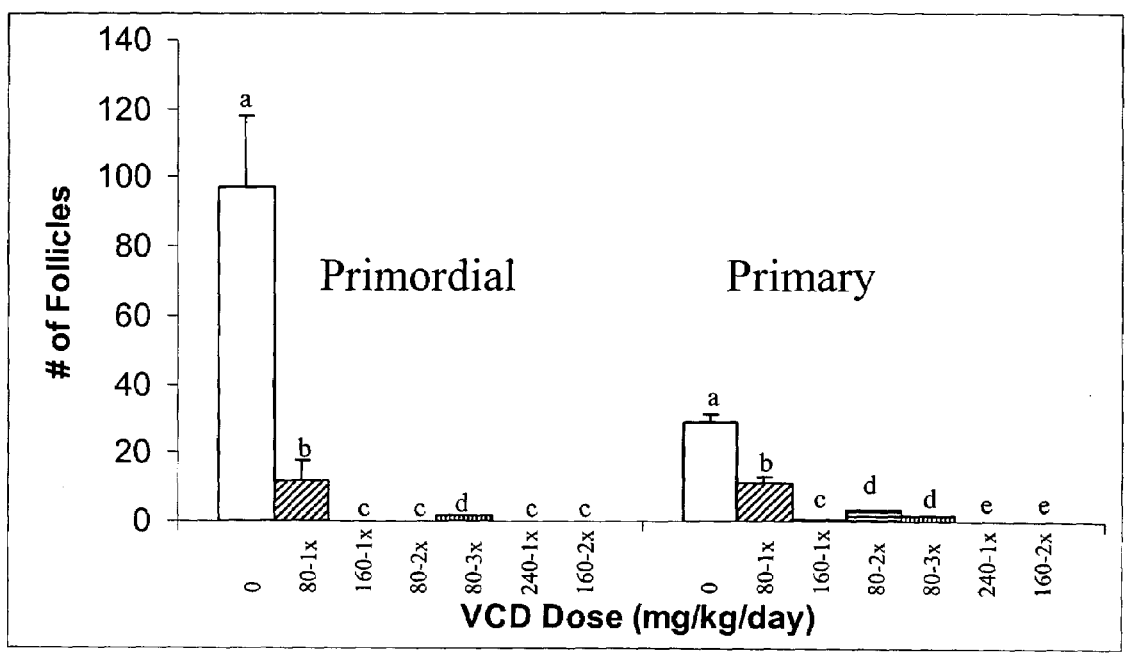
FIG. 1: Effect of treatment with VCD on numbers of primordial and primary follicles in mice. Female B6C3F$_1$ mice (28 days of age) were injected (i.p.) with sesame oil control or VCD 80 mg/kg (1, 2, or 3 times, ×, daily), 160 mg/kg (1 or 2× daily), or 240 mg/kg (1× daily) for 15 d. Ovaries were collected on d15 following onset of treatment and processed for histological evaluation as described in the Examples below. Values represent mean number of follicles in the total of every 20$^{th}$ section ±SEM; n=6 per group, different letters within a follicle type, different from one another (p<0.05).

The present invention is based, in part, on the discovery that VCD induces ovarian failure by acceleration of atresia in female animals and produces, at most, only minimal effects on other body organs and physiological pathways. In addition, if sufficient time is allowed to pass, these animals develop one or more characteristics of perimenopause or menopause. Thus, as discussed below, other than a reduction in ovarian and uterine weight, there are no other direct irreversible effects observed at the tissue level. Subsequent physiological conditions that arise will be the consequence of ovarian failure.

As a result, these animals can be used as a model for human perimenopause and menopause. Such a model system is dramatically superior to animal models based on ovariectomy, irradiation, or genetic manipulation. In addition, the procedures described herein can be used to provide a method for non-surgical induction of ovarian failure to control the populations of domestic and wildlife animals. A key feature of the animals of the present invention is that they contain their ovaries, i.e., the animals have not been subjected to ovariectomy. Therefore, the animals of the present invention contain at least one functional ovary, and preferably all of them.

As used herein the term "perimenopause" refers to a condition that precedes menopause in which ovarian cyclicity becomes irregular, FSH levels become elevated, and ovarian 17β-estradiol levels become erratic. In women this can be up to 10 years before menstruation ceases. The term "menopause" as used herein refers to the time at which complete ovarian failure has occurred. This is when menstrual periods have ceased, LH and FSH levels are elevated and 17β-estradiol levels have plummeted. Thus, the characteristics of perimenopause and menopause include those described above.

For perimenopause, histological evaluation of ovarian sections reveals a complete absence of primordial follicles, and reductions in larger preantral and antral follicles. At that time, circulating FSH levels become elevated, and ovarian cyclicity has become irregular as determined by vaginal cytology. In addition, there is a loss of bone mineral density and a reduction in ovarian weight that begins in perimenopause and can continue during menopause. For menopause, all ovarian follicles are depleted, circulating FSH levels have plateaued, and the animals are acyclic.

The model animal of the present invention is a mammalian non-human female. Suitable animals include laboratory and research primates and rodents. Specific examples of suitable animals include dogs, cats, hamsters, rabbits, sheep, cattle, deer, elk, moose, pigs, goats, ferrets, horses, monkeys, chimps, rats, mice. Rats and mice are especially preferred.

Transgenic, gene-deficient (i.e., knock-out), or knock-in animals, particularly mice, are especially preferred for the study of certain conditions. The purpose of using these animals is that they model human disease states which are associated relevant to the onset of perimenopause and/or menopause. Preferred examples are mice and rats which have been modified in a property which is relevant to the changes in the body upon the onset of menopause and/or during menopause. Specific examples of such animals include those with modifications in apo e, apob, LDLR, LCAT, $A^Y$, $Foxnl^{nu}$, Bmp4, Kit, ERKO, BERKO, OB/OB, and Aβ.

The present invention also provides methods of preparing the animal model. VCD appears to be the active agent in producing the depletion of ovarian primordial follicles, or at least serves a precursor to the actual active species in vivo. Therefore, VCD may be administered to the animals. Since VCH is converted to VCD in vivo, VCH may also be used in the present invention. The pathway from VCH to VCD appears to involve the formation of VCH-1,2-epoxide and/or VCH-7,8-epoxide. See Fontaine et al., Drug Metabolism and Disposition, 29, 179-184, 2001, FIG. 1 of which is incorporated herein by reference. Therefore, VCH-1,2-epoxide and/or VCH-7,8-epoxide may also be administered in order to produce the animal of the present invention. In principle, any agent that is converted to VCD (or the actual active agent produced therefrom) in vivo may be used to prepare the animal model.

As described by Fontaine et al. (see especially FIG. 1), VCH is a chiral compound and each enantiomer is converted into epoxide products having differing stereochemistry. All of these stereoisomers may be used in the present invention. Thus, the compound used may be (S)-VCH, (R)-VCH, (S)-VCH-1,2-expoxide, (R)-VCH-1,2-expoxide, (S)-VCH-7,8-expoxide, (R)-VCH-7,8-expoxide, (S)-VCH-diepoxide, (R)-VCH-diepoxide, and any mixture thereof. VCD, VCH, and VCH-1,2-epoxide are available from Aldrich Chemical Co.

The dosing of the compound, in terms of both dosage amount and method of administration, may vary widely. The compound is administered at a sufficient dosage to cause at least partial depletion of the ovarian primordial follicles. In so doing, a sufficient amount of time is permitted to elapse so that the animal develops at least one characteristic of perimenopause or menopause. Thus, the production of the animal model depends on the method of delivery, the dosage amount, and the time that the dose is administered. For example, a continuous dose administered via an implant (discussed in more detail below) may use less VCD over the same time period as compared to repetitive i.p. injections.

In general, VCD is more potent than VCH and therefore may be used at a lower dose. The potency of VCH-1,2-expoxide and VCH-7,8-expoxide is expected to be between VCH and VCD.

In one embodiment, VCD is administered at a dose of at least 80 mg/kg per day. One preferred range is 80-720 mg/kg per day. This range includes all specific values and subranges therebetween, such as 90, 100, 150, 200, 250, 300, 350, 400, 450, 500, 550, 600, 650, and 700 mg/kg per day. One preferred subrange is 100 to 160 mg/kg/day. This range includes all specific values and subranges therebetween, such as at least 110, 120, 130, 140, 150, and 160 mg/kg/day. The preferred time period for administering VCD is at least 10 days, preferably 10 to 30 days, or more. In a preferred embodiment, VCD is administered intraperitoneally (i.p.). In another embodiment, VCD is administered using an implant with a slow time release over several days.

A suitable dosage of VCH is at least 900 mg/kg/day. Preferably the maximum dose is at most 1600 mg/kg/day. This range includes all specific values and subranges therebetween, such as 1100, 1200, 1300, 1400, and 1500 mg/kg/day. The preferred time period for administering VCH is at least 6 days, preferably 10 to 30 days, or more. In a preferred embodiment, VCH is administered intraperitoneally (i.p.). In another embodiment, VCD is administered using an implant with a slow time release over several days.

Administration of the compound may be through any of the following routes: intraperitoneal injection, subcutaneous injection, lavage, oral intake, dermal patch, dermal application, dermal injection, inhalation, intravenous injection, transplacental exposure, intravaginal implant, subcutaneous implant, nasal spray, or implant dart. The exact dosage for any particular method of administration can be determined readily using techniques well-known in the art. A preferred example of a subcutaneous implant is a minipump, particularly an Alzet minipump. The implant may be biodegradable or non-biodegradable. Preferably, for use a population control device, the implant is biodegradable. For animals used a research models, the implant is preferably non-biodegradable.

A variety of different vehicles may be used to administer the compound. Examples of suitable vehicles include physiologically acceptable oils (e.g., sesame oil, corn oil, and mineral oil), DMSO, acetone, and mixtures thereof.

Some routes of administration may be more effective in a commercial setting as compared to other methods. For example, using a subcutaneous implant may be more cost-effective in terms of animal handling and storage and personnel costs associated with producing the animal in commercial quantities.

The animal model of the present invention may be used in a wide variety of assays of screening agents for their potential effect on a perimenopausal or menopausal female. In this embodiment, the agent is administered to the animal and the effect on the animal is evaluated. For example, the model can be used to evaluate, i.e., screen, potential therapeutic agents for preventing or treating conditions associated with perimenopause and menopause. In this embodiment, the agent is administered to the animal and evaluated for its effect.

These types of screens are routine in the art. What the present invention provides is a novel model with which to perform the testing. For an example of a procedure for using an animal model of human perimenopause and/or menopause to screen agents, see the ovariectomized mouse model for human menopause described in U.S. Pat. No. 6,583,334, the contents of which are incorporated herein by reference.

Transgenic, gene-deficient, or knock-in animals are particularly preferred in some aspects of this embodiment. Here, the effect of a genetic modification can be studied in isolation, i.e., no external agents are administered to the animal, or the effects of a potential therapeutic agent can be evaluated as described above. Specific examples of conditions include hot flashes, osteoporosis, incontinence, poylcystic ovarian disease, Alzheimer's disease, depression, macular degeneration, arthritis, anxiety, obesity, ovarian cancer, diabetes mellitus, vaginal dryness, vaginal discharge, cancers of the reproductive tract, breast cancer, thinning of the skin, loss of libido, colorectal cancer, alopecia, hirsutism, cardiovascular disorders (which include heart attack, stroke, deep vein thrombosis, hypertension, hypotension, ischemia, pulmonary embolism, atherosclerosis, heart abnormality, hypercholesterolemia, hypertriglyceridemia, hypocholesterolemia, hypotriglyceridemia, vascular defects, vascular homeostasis, and sudden cardiac death), loss of manual dexterity, osteopenia, cognitive impairments, dementia, etc.

The present invention also provides a method of inducing ovarian failure in a mammalian non-human female animal other than a mouse or a rat, comprising administering to the animal an effective amount of the compound. Suitable animals include those discussed above suitable dosage for this purpose is at least 90 mg/kg per day of VCD for a time sufficient to induce ovarian failure. VCH can also be used for this purpose, for example, at the dosages described above.

The compound may also be used to control the size of a non-human animal population, comprising administering an effective amount of the compound to the animal population sufficient to cause at least partial ovarian failure in at least a portion of the female members of the animal population. Such animals include dogs, cats, hamsters, ferrets, rabbits, sheep, cattle, horses, pigs, deer, elk, moose, bears, goats, monkeys, wild felines.

In this embodiment, administration of the compound may be through any of the following routes: intraperitoneal injection, subcutaneous injection, lavage, oral intake, dermal patch, dermal application, dermal injection, inhalation, intravenous injection, transplacental exposure, intravaginal implant, subcutaneous implant, nasal spray, or subcutaneous dart.

The present invention also provides a solid composition suitable for oral administration, comprising the compound and a solid excipient. Preferably, such a composition is in the form of a pill, capsule, or caplet that can be administered to animals and humans. Solid excipients which are suitable for orally administerable compositions are well-known. For a description, see *Kirk-Othmer Encyclopedia of Chemical Technology*, Fourth Edition, Volume 18, p. 491-502 (1996), incorporated herein by reference.

The composition may also be in the form of a dermal or subcutaneous implant. Such a composition contains the compound in a suitable dermal or subcutaneous deliver device. Such devices are well-known in the art, see *Kirk-Othmer Encyclopedia of Chemical Technology*, Fourth Edition, Volume 8, p. 445-474 (1996), incorporated herein by reference. In another embodiment, an implant dart could be used for wildlife population control.

Figure 2:
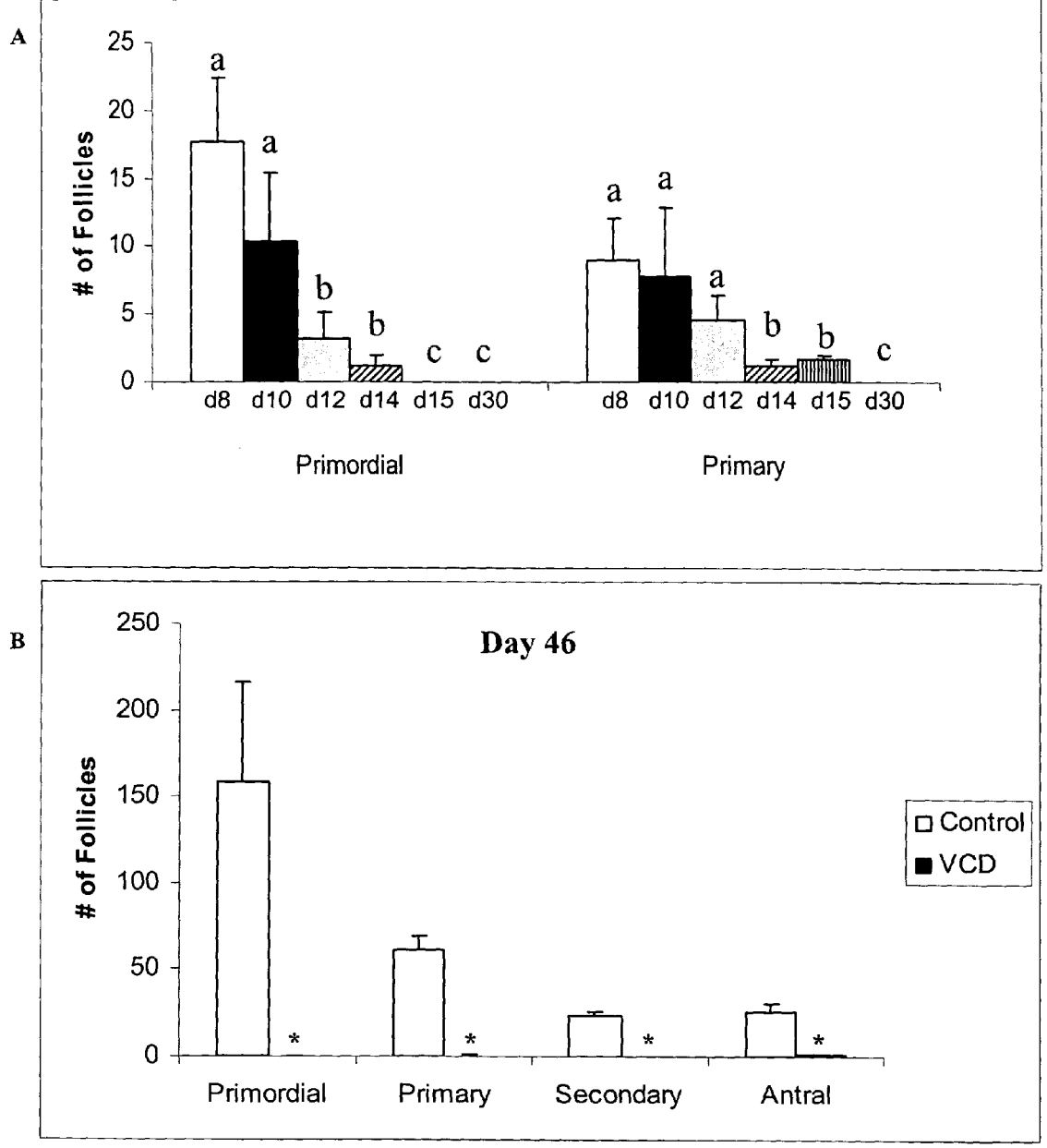
FIG. 2: Effect of VCD-induced follicle loss over time. Female B6C3F$_1$ mice (28 days of age) were injected daily with VCD (160 mg/kg, i.p. 1×) or sesame oil control for ≦15 d. Ovaries were collected (d8-d46) following onset of treatment and processed for histological evaluation. Oocyte-containing follicles were classified and counted as described in the Examples below. A) d8-30, primordial and primary follicles; B) d46 primordial, primary, secondary and antral follicle numbers. Values represent the mean total number of follicles counted in every 20$^{th}$ section of each ovary ±SEM; n=4 per group, *p<0.05 or different letters within a follicle type, different from one another (p<0.05).
Figure 3:
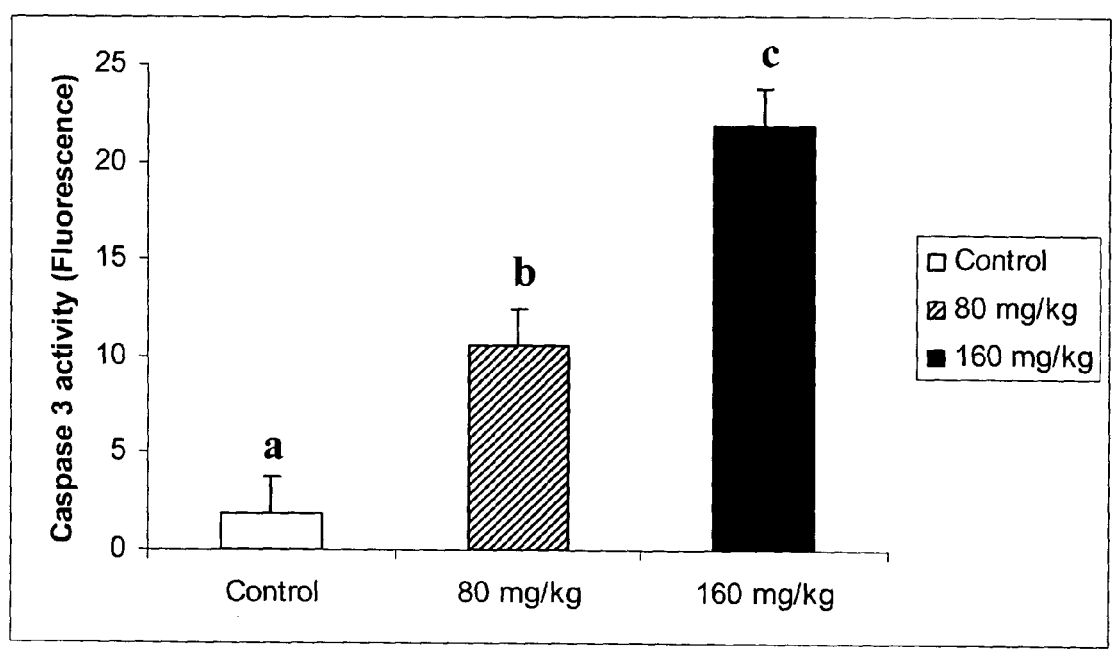
FIG. 3: Effect of VCD treatment on Caspase 3 activity in primordial and primary follicles. Female B6C3F$_1$ mice (28 days of age) were injected daily with VCD (80 or 160 mg/kg, i.p.) or sesame oil for 10 d. Ovaries were collected 4 hours following the final treatment of VCD. Small pre-antral follicles were isolated, and caspase-3 activity determined as described in the Examples below. Data are represented as group mean values, n=2 replicates per group of 6 ovaries, different letters within a treatment concentration, different from one another (p<0.05.
Figure 4:
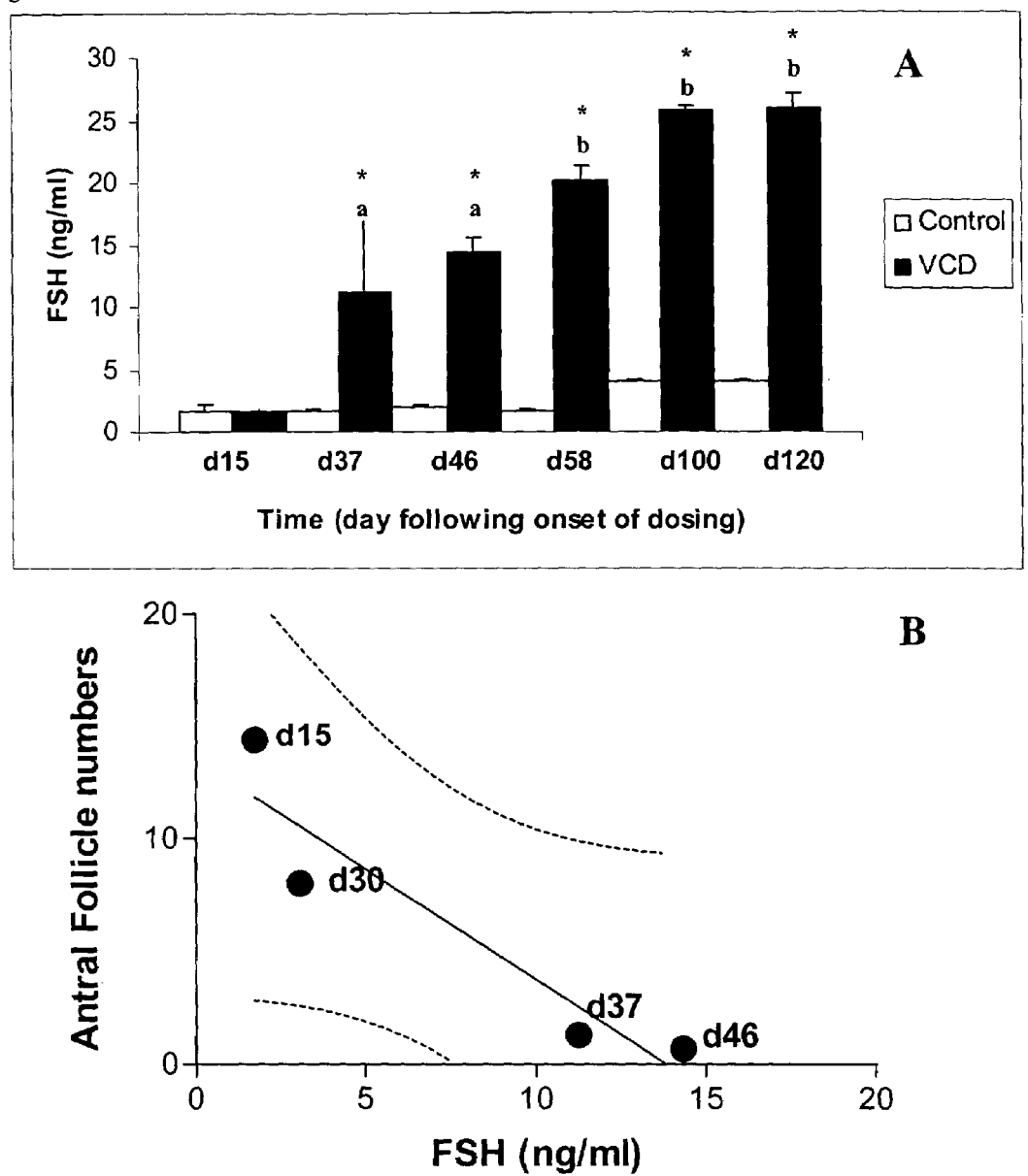
FIG. 4: Effect of VCD treatment on circulating levels of FSH and antral follicles. Female B6C3F1 mice (age 28 days) were injected daily with sesame oil or VCD (160 mg/kg, i.p., 1×15 d). A) Plasma was collected on d15, d37, d46, d58, d100 and d120 following onset of treatment for 15 d for determination of FSH content as described in the Examples below. (n-6-18 per group, *p<0.01 different from control different letters within a treatment, different from one another p<0.05). B) Ovaries were collected on d15, d30, d37, and d46 and processed for histological evaluation as described in the Examples below. Antral follicles were counted in every 20$^{th}$ section and a regression analysis was performed to compare circulating levels of FSH vs Antral follicle number (n=6-12 per group, r$^2$=0.87, p<0.02).

Because of the potential benefits of utilization of transgenic and gene-deficient mice developed to investigate specific pathologies associated with perimenopause and/or menopause, mice were chosen for the initial development and characterization of the model of VCD-induced ovarian failure. In developing a model for menopause, it is critical to induce follicle loss in a timely manner to provide sufficient time for long-term studies. Preliminary experiments in immature d28 B6C3F$_1$ mice were conducted using an increased dosing regimen to more rapidly accelerate the rate of follicle loss (FIG. 1). A time course was conducted to determine the minimum amount of dosing conditions necessary to fully deplete the ovary of primordial follicles in B6C3F$_1$ mice without producing adverse physiological side effects (FIG. 2). Animals were treated daily with VCD via injection at 160 mg/kp/day i.p. or sesame oil for 15 days. Animals were killed, tissues harvested, and serum collected on d1-15, d37, d46, d58, d120, and d127 following the onset of dosing. To verify that follicle loss in this dosing regimen is also via atresia, the activity of caspase 3, an enzyme involved in the apoptotic pathway, was measured in small preantral follicles isolated as described in Hu et al. (18) following 10 d of dosing (FIG. 3). Caspase-3 activity was increased ($p<0.05$) in small pre-antral (primordial and primary) follicles isolated from VCD-treated (14.37 flourescent units/40 μg protein ±4.9) relative to control (1.87 flourescent units/40 μg protein ±0.53) mice indicating that the number of follicles undergoing atresia was increased. Thus, the increased dosing regimen with VCD relative to 80 mg/kg/day (the dose previously used to characterize VCD-induced follicle loss) did not impair intracellular apoptotic signaling as would result if a toxic, necrotic response had occurred. The morphological appearance of primordial and primary follicles in VCD-treated animals on d10 was also indicative of atresia via apoptosis. From this experiment, the optimal dose of VCD was determined for 15 d and subsequent experiments were conducted using that dosing regimen. To determine the impact of loss of primordial follicles on ovarian function, antral follicles were counted and circulating FSH levels measured on d15-d127 (FIG. 4). There was an inverse correlation ($p<0.02$) between these two parameters. This is indicative of impending ovarian failure resulting from loss of large antral follicles. Throughout the experiment several physiological parameters were measured. Body and tissue weights were evaluated. The onset of vaginal opening (31±0.5 days), whole body weights and adrenal, spleen and kidney wet-tissue weights were not affected by VCD treatment at any time-point. The modest increases in ($p<0.05$) liver weights seen in VCD-treated animals on day d15 (10% above control) and d37(15% above control), however by d46, liver weights had returned to control levels. The modest increases ($p<0.05$) in liver weights seen in VCD-treated animals during the period of exposure was because of activation of metabolic mechanisms. Circulating liver enzymes aspartate aminotransferase (AST) and plasma alanine aminotransferase (ALT) in VCD-treated animals were not different from controls at any time d1-d46 ($p>0.05$). Hepatocellular vacuolar degeneration (a pathologic lesion consistent with mild hepatocellular toxicity) was evaluated by the University Animal Care Diagnostic Laboratory of the Ariz. Health Sciences Center. There was no difference in the occurrence of these lesions in naive, vehicle-treated control, or VCD-treated mice at any time. Ovarian tissue weights were not significantly different across treatment groups on d10, or d15, however, by d37, VCD-dosed animals displayed significantly reduced ovarian weights compared to controls. Uterine weights were also reduced by VCD treatment by d15. The reduced uterine weight likely obviously resulted from lower ovarian 17β-estradiol, and, therefore, the loss of its lack of well-known tropic effect on the uterus. The decrease in ovarian and uterine weights is consistent with that seen at 360 d in the long term studies in mice and rats and is indicative of ovarian failure; loss of large antral follicles and ovarian and uterine atrophy (15, 22). Collectively, these observations demonstrate that after 15 d of VCD dosing, ovarian and uterine weight reductions are the only direct irreversible physiological effects observed at the tissue level. Both of these findings are consistent with ovarian failure in menopausal women. Furthermore, no toxicity or impact on liver function was measured in blood or observed morphologically. It can therefore be assumed that the development of any subsequent adverse physiological conditions is the result of ovarian failure.

It is to be noted that in any embodiment of the invention described above, 4-vinylcyclohexene diepoxide, 4-vinylcyclohexene, 4-vinylcyclohexene-1,2-epoxide, and 4-vinylcyclohexene-7,8-epoxide as described above can be used alone as the agent for inducing ovarian failure. Alternatively, these compounds can be used together in any desired ratio.

EXAMPLES

Having generally described this invention, a further understanding can be obtained by reference to certain specific examples which are provided herein for purposes of illustration only and are not intended to be limiting unless otherwise specified.

Example 1

Treatment with VCD reduced ($p<0.05$) the number of primordial and primary follicles 15 d following commencement of treatment in a dose-dependent manner in $B6C3F_1$ mice (FIG. 1). Primordial follicles were reduced at 80 mg/kg to 12.1% of control, 160 mg/kg (80 mg/kg, 2× daily, and 160 mg/kg 1× daily) 0% of control, 240 mg/kg (80 mg/kg 3× daily) 2.1% of control, 240 mg/kg (240 mg/kg 1× daily) 0% of control, and 320 mg/kg (160 mg/kg 2× daily) 0% of control. Primary follicles were reduced at 80 mg/kg to 38.6% of control, 160 mg/kg (160 1× daily) 2.8% of control, 160 mg/kg (80 mg/kg 2× daily) 11.3% of control, 240 mg/kg (80 mg/kg 3× daily) 5.1% of control, 240 mg/kg (240 mg/kg 1× daily) 0% of control and 320 mg/kg (160 mg/kg 2× daily) 0.6% of control.

Treatment with VCD (160 mg/kg, i.p.) for =15 days reduced ($p<0.05$) primary and primordial follicle numbers progressively over time (FIG. 2A). By d46 following commencement of 15 d of treatment, all follicle pools were substantially depleted ($p<0.05$) relative to control. There were no primordial follicles and primary, secondary and antral follicles were 0.5%, 0.7%, and 2.6% of control values respectively (FIG. 2B).

During the initiation of apoptosis, the executioner caspases (caspase-3) become activated which results in cellular collapse. Mice were given daily injections of VCD (160 mg/kg, or 80 mg/kg, i.p.) for 10 d. Four hours after the final treatment, small preantral follicles were isolated and activity of the apoptosis-associated executioner protease enzyme caspase-3 was measured. Relative to controls, increased ($p<0.05$) cleavage activity of caspase-3 in isolated small pre-antral follicles was observed in a dose-associated manner (FIG. 3).

The optimal concentration of VCD for primordial follicle loss (lowest amount, shortest time) was determined to be 160 mg/kg, injected 1× daily (resulting in complete loss of primordial follicles). Daily treatment for 15 d with VCD (160 mg/kg) subsequently resulted in a progressive reduction ($p<0.05$) of ovarian weights on d37 (71.2% of control), d46 (61.8% of control) and d120 (20.7% of control) following the onset of treatment (Table 1). Additionally, uterine weight relative to age-matched vehicle controls was reduced ($p<0.05$) on d15 (66.04%), d37 (71.8%), and d120 (47.0%). There was no effect of VCD treatment on adrenal, kidney or spleen weight at any time. A modest increase ($p<0.05$) in liver weight was observed on d15 (10% above control) and d37 (15% above control). These weights had returned to control levels by d46. Because VCD can be metabolized by the liver, liver function was investigated by measurement of the liver enzymes aspartate aminotransferase (AST) and alanine aminotransferase (ALT) and hepatocellular vacuolar degeneration was evaluated (Table 2). Plasma samples were collected on d1-d46 (following 15 d of treatment) and circulating levels of ALT and AST were determined to be within the normal range for this strain of mice. Further, to assess hepatic effects on circulating lipid profiles, total plasma cholesterol, HDL and triglycerides were determined for d10, d15 and d37 following the onset of treatment (Table 2). All lipid fractions were within the normal range for this species, and did not differ ($p<0.05$) from control.

VCD treatment (160 mg/kg, 1 Sd) resulted in increased circulating levels of FSH compared to controls over time (FIG. 4A). On d37 following the onset of treatment, plasma FSH levels were increased ($p<0.05$) in VCD-dosed animals (11.5±5.7 ng/ml) relative to control (1.7±0.06 ng/ml), with a continued increase on d46 (VCD: 14.3±1.3 ng/ml), d58 (VCD: 20.2±1.2 ng/ml), d100 (VCD: 25.8±0.23 ng/ml), and d120 (VCD: 25.9±1.1 ng/ml) Plasma FSH levels on d127 (data not shown) was increased ($p<0.05$) relative to controls, however, not increased relative to d100 and d120 values indicating a plateau in circulating FSH.

Antral follicle numbers were progressively reduced (d15-d46; $p<0.05$) as a result of VCD treatment (160 mg/kg, 15 d) and negatively correlated ($r^2=0.87$) with increasing circulating levels of FSH on those days (FIG. 4B). Because antral follicles had become depleted, d58 and subsequent time points are not included in the analysis.

Figure 5:
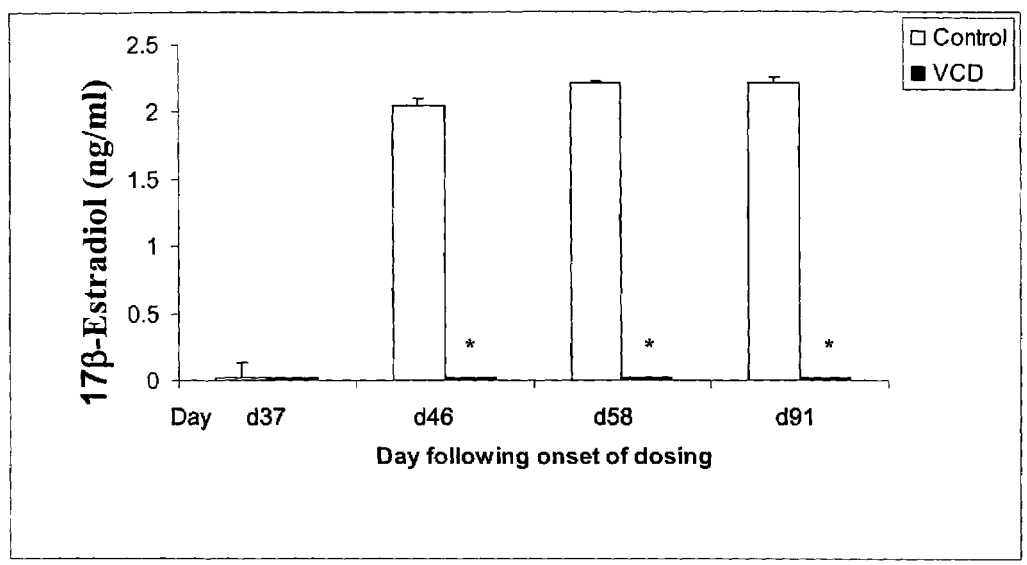
FIG. 5: Effect of VCD treatment on circulating levels of 17μ-estradiol. Female B6C3F1 mice (age 28 days) were injected daily with sesame oil vehicle or VCD (160 mg/kg, i.p., 1×, 15 d). Plasma was collected and pooled from a minimum of 12 animals per groups on d37, d46, d58 and d91 following the onset of treatment and concentration of 17β-estradiol was determined as described in the Examples below. (n=3 pools, *p<0.01 different from control).
Figure 6:
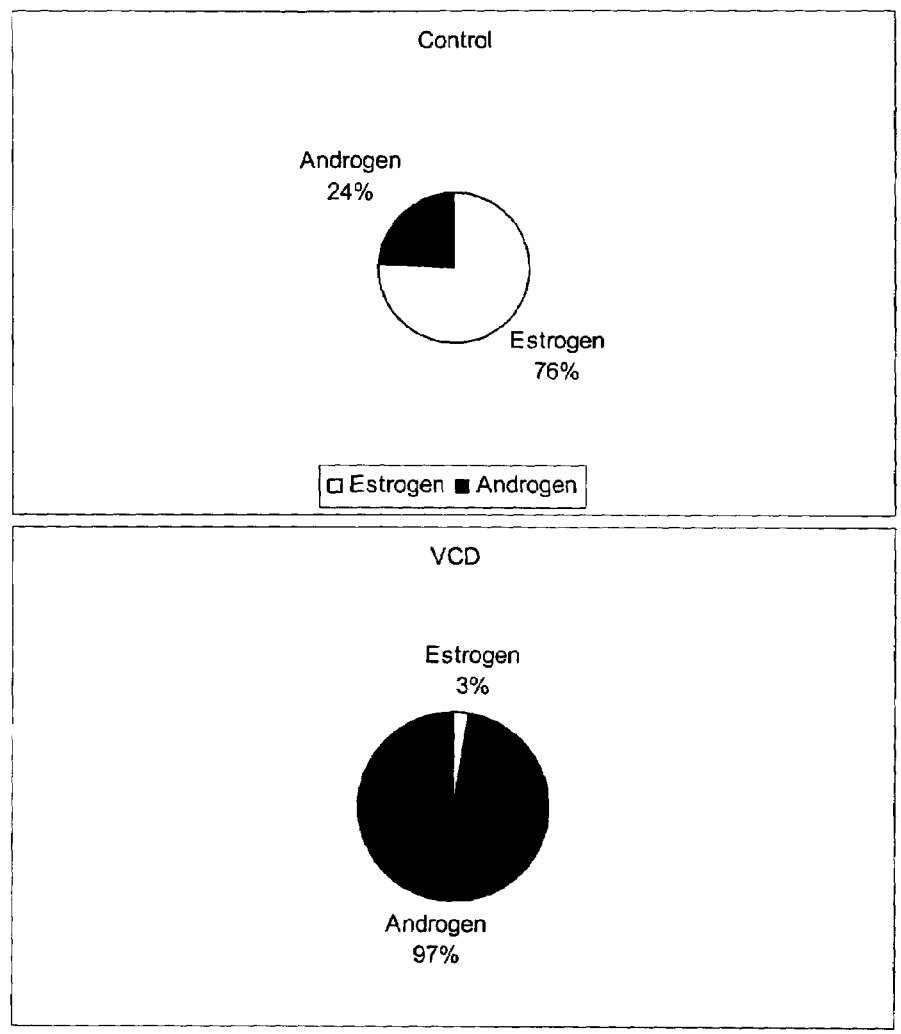
FIG. 6: Relative amounts of circulating 17β-estradiol and androstenedione on d46 following the onset of treatment. Female B6C3F1 mice (age 28 days) were injected daily with sesame oil vehicle or VCD (160 mg/kg, i.p., 1×, 15 d). Plasma was collected and pooled from a minimum of 12 animals per group on d46 and concentration of 17β-estradiol and androstenedione was determined as described in the Examples below. (n=3 pools).

Plasma levels of 17β-estradiol in VCD-treated animals were below the limit of detection in VCD-treated groups on d37 and remained at that level through d91 (FIG. 5). Conversely, in control animals circulating 17β-estradiol began to increase ($p<0.05$) on d 46 (2.05 pg/ml), d57 (2.21 pg/ml) and d91 (2.21 pg/ml). Circulating levels of androstenedione in plasma pools from VCD-treated animals were similar to controls on d46 (control 0.64±0.01; VCD: 0.73±0.05 ng/ml). Because of this, there was an increased relative abundance of androgen versus estrogen (FIG. 6; control: 24%; VCD: 97% of androgen plus estrogen).

VCD treatment (160 mg/kg, i.p.) resulted in disruption of estrous cyclicity. The mean cycle length was determined in control animals to be 4.49±0.48 d. Animals with cycle lengths less than 3 d or greater than 5 d were determined to be irregular. Cycle length was disrupted in VCD-dosed animals beginning on d15 (7/24, irregular) and by d58 all animals were acyclic. Control animals consistently maintained regular cycles across all time points.

Figure 7:
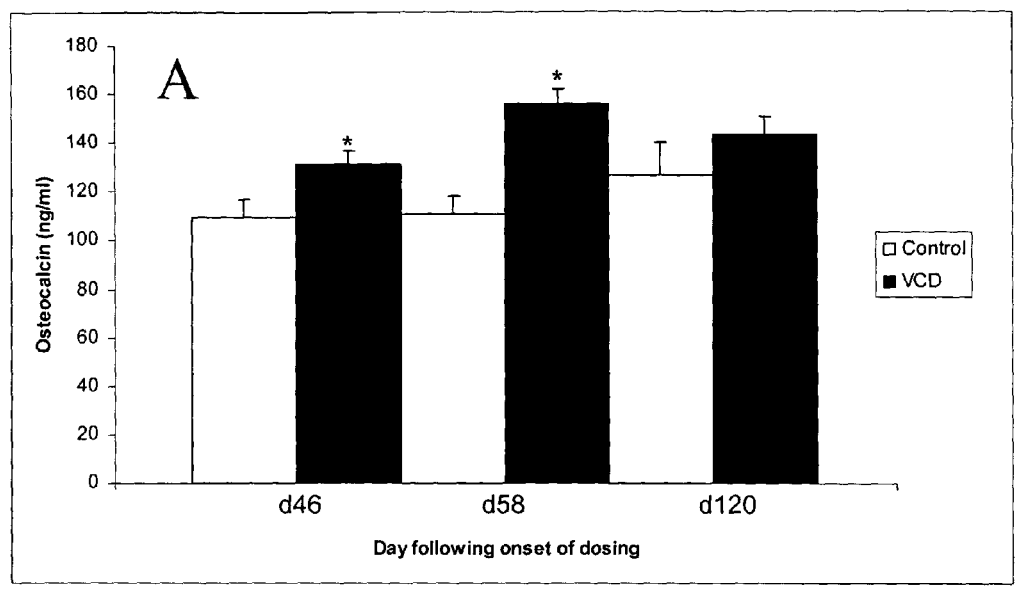
FIG. 7: Effect of VCD treatment on circulating levels of Osteocalcin and bone histomorphometry. Female B6C3F1 mice (age 28 days) were treated daily with sesame oil or VCD (160 mg/kg, i.p., 15 d). Plasma was collected on d46, d58, and d120 and concentration of osteocalcin was measured as described in the Examples below. Data are represented as a group mean values ±SEM (n=6-10 per group, *p<0.05). Photomicrographs of representative femurs collected on d58 from B) VCD-treated and C) control animals, prepared for histological evaluation as described in the Examples below. Arrows indicate distance from growth plate to distal metaphysis of femur (n=6; Magnification 40×).
Figure 7:
Figure 7:
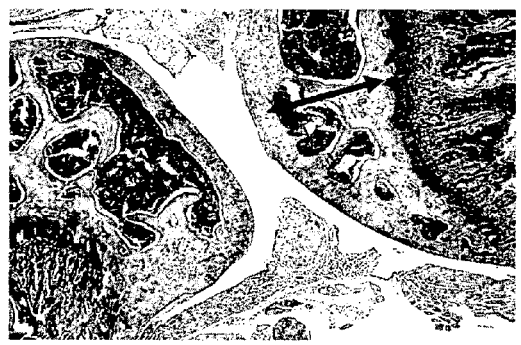

Osteocalcin is a protein produced in osteoblasts and is increased in circulation under conditions of increased bone turnover. Plasma levels of osteocalcin were increased ($p<0.05$) in VCD-treated (160 mg/kg, i.p., 15 d) groups relative to control on d46 (control: 109.6±7.0, VCD: 131.3±5.4 ng/ml), and d58 (control: 111.2±6.9, VCD: 156.3±6.1 ng/ml FIG. 7A). By d120 the two groups were not different (control: 127.1±12.7, VCD; 143.4±7.1 ng/ml; FIG. 7A). Femora collected on d58, from VCD-treated animals (160 mg/kg, 15 d, FIG. 7B) displayed enhanced distances from growth plate to distal metaphysis of the femur with increased lucane relative to controls (FIG. 7C).

Figure 8:
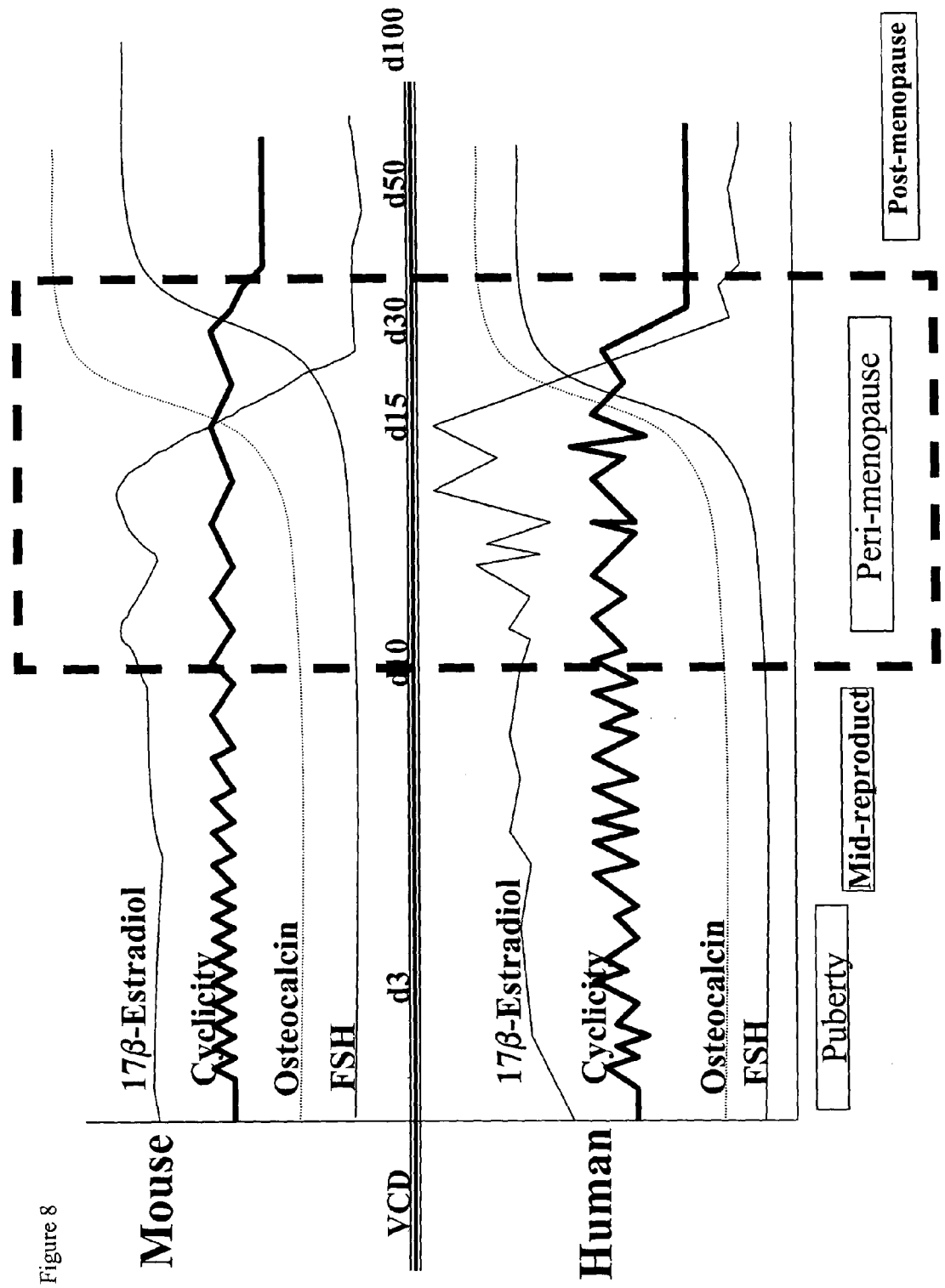
FIG. 8: Comparison of changes in reproductive parameters between VCD-dosed mice and women as they approach menopause. Summarized patterns of cyclicity and hormone levels measured in VCD-treated mice are compared with those values reported in women. Values for mice are assigned day (d) relative to the onset of treatment, (d1) with VCD for 15 d.

FIG. 8 is a comparison of the patterns of cyclicity, circulating levels of FSH, osteocalcin, and 17β-estradiol between VCD-treated mice (d1-d100) and values published for similar stages of reproductive function in women. For example, in women, puberty is equivalent to d3 following the onset of treatment in mice, and peri-menopause can be compared to d10-d50, with post-menopause resembling d50-d100.

Materials and Methods

Animals: Immature female $B6C3F_1$ mice (21 days) were obtained from Harlan Laboratories (Indianapolis, Ind.), housed in plastic cages, and maintained on 12 hour light-dark cycles at 22±2° C. Animals were allowed to acclimate to the animal facilities for 1 week prior to initiation of treatment. Food and water were available ad libitum. All experiments were approved by the University of Arizona Institutional Animal Care and Use Committee and conformed to the Guide for the Care and Use of Experimental Animals.

Treatment: Immature mice (d28) were weighed and injected i.p. with either 80 mg/kg (1, 2, or 3 times daily), 160 mg/kg (1 or 2 times daily), or 240 mg/kg (once daily) with VCD or sesame oil (vehicle control, i.p.) for 15 d resulting in a total daily exposure of 80, 160, 240, or 320 mg/kg (n=6/group). All reagents were obtained from Sigma-Aldrich (St. Louis, Mo.). Estrous cycles of each animal were monitored daily by vaginal cytology from date of vaginal opening to persistent diestrus in VCD-treated mice, and from date of vaginal opening to d120 in controls. On d8, d10, d12, d14, d15, d30, d37, d46, d57 and d120, animals were weighed, euthanized by $CO_2$ inhalation, and the ovaries, liver and trunk blood were collected. Plasma was separated from whole blood and stored at $-20°$ C., and liver tissues were stored at $-80°$ C. At each time point, adrenals, kidneys, uteri, ovaries, liver, and spleen were removed, grossly examined for lesions and wet tissue weights were recorded. Additional blood samples were collected by retro-orbital puncture and plasma was collected and stored on d58, d79, d91, and d100.

Histology and oocyte counting: Ovaries were trimmed of fat and placed in Bouin's fixative (2 hours), transferred to 70% ethanol, paraffin-embedded and serially sectioned (4-5 µm), mounted and stained with hematoxylin and eosin. In every $20^{th}$ section (10-13 sections per ovary), pre-antral follicles were classified as primordial (oocyte surrounded by a single layer of flattened granulosa cells), primary (oocyte surrounded by a single layer of cuboidal cells), secondary (oocyte surrounded by multiple layers of granulosa cells) or antral follicles (follicles containing a fluid-filled antrum). Femora were collected on d58 from both control and VCD-treated animals, fixed in 4% paraformaldehyde, transferred to formaldehyde/formic acid (Cal-Rite, Richard Allan Scientific, Kalamazoo, Md., decalcified 24 hours, vacuum embedded in paraffin and 4.5 µm sections of distal metaphysis were prepared and stained with hematoxylin and eosin.

Follicle Isolation: Small preantral follicles (fraction 1, 25-100 µm in diameter), were prepared by gentle enzymatic dissociation of ovaries and hand sorting with micropipettes. Pools of follicles were prepared from both ovaries of six mice in each treatment (control or VCD) for each observation. Following isolation, follicles were washed twice with M199 medium and stored at $-20°$ C.

Hormone Assays: Plasma FSH was measured by radioimmunoassay (RIA). Rat FSH hormone antigen, rat FSH antiserum and mouse FSH reference preparation were purchased from the National Institute of Diabetes and Digestive and Kidney diseases. Iodination reagents (Iodo-Beads™28665, 28666) were purchased from Pierce (Rockford Ill.). Briefly, a standard curve was prepared and cold standards and samples (100 µl) were added to labeled tubes along with primary antibody (1:1400 dilution) and iodinated FSH. Samples were shaken and stored at 4 C overnight. On day 2, 100 µl secondary antibody (Sigma Chemical, cat. # R9133) was added (1:10) dilution along with 200 µl of 2% normal rabbit serum and incubated at room temperature for 5 minutes. Tubes were centrifuged for 15 minutes at 3000 rpm, supernatant was decanted and pellets were counted in a gamma counter for 1 minute each. All samples were run in duplicate. The mean sensitivity of the assay was 200 pg/ml and inter- and intra-assay coefficients of variation were 2.7% and 6.7% respectively. Plasma 17β-estradiol was measured in unextracted plasma by radioimmunoassay (Diagnostic Products Inc., CA). The mean sensitivity of the assay was 5.1 pg/ml. The intra-assay coefficient of variation was 5.3%. Circulating androstenedione was measured by specific RIA. Androstenedione standards and antibody were provided by Dr. Cheryl Dyer (Northern Arizona University). The mean sensitivity of the assay was 70 pg/ml with an inter-assay coefficient of variation of 5.3%. The results of all RIAs were calculated by four-parameter logistic analysis using the software AssayZap (BioSoft, Ferguson, Mo.). Results are the mean±SEM.

Assessment of Hepatic Function: Hepatocellular vacuolar degeneration and enzymatic activity of circulating aspartate aminotransferase (AST) and alanine aminotransferase (ALT) were determined by the Diagnostic Laboratory of the Arizona Health Sciences Center. Total cholesterol and triglycerides were quantified using Sigma reagents 401-25P and 344-20 respectively. HDL was measured by precipitating apoB-containing lipoproteins (Boehringer Mannheim reagent 543004) and assaying cholesterol in the supernatant fraction using the Sigma 401-25P reagent.

Caspase-3 Protease Activity Measurement: The cleavage activity of caspase-3 was measured by a fluorescent activity assay. Briefly, the enzymatic reaction was carried out at 37° C. in protease assay buffer (20 mM HEPES, 100 mM NaCl, 10 mM dithiothreitol, 1 mM EDTA, 0.1% [w/v] 3-3 ([3-cholamidopropyl] dimethylammonio)-1-propanesulfanate, and 10% sucrose pH 7.2). Cellular protein (60-180 µg) was incubated with 50 µM of caspase-3 substrate, DEVD-AMC, at 37° C. for 60 minutes. Substrate cleavage was detected by measurement of the fluorescence of free 7-amino-4-methylcoumarin (AMC) with an F-2000 fluorescence spectrophotometer (Hitachi, Ltd., Tokyo, Japan) at 460 nm emission upon excitation at 380 nm.

Osteocalcin measurement: Intact serum Osteocalcin was measured using an immunoradiometric assay (IRMA, Immutopics, San Clemente, Calif.). Assay sensitivity was 0.4 ng/ml and the intra-assay coefficient of variation was 6.7%.

Data Analysis: Oocyte numbers were determined in ovaries from individual animals, averaged, and the means (±SEM) in control versus treated animals were analyzed for significant differences by one-way analysis of variance (ANOVA) with significance set at $p<0.05$. Post-hoc tests (Tukey-Kramer) were used where appropriate. The differences in plasma hormone concentrations among treatments were analyzed using a one-way ANOVA. The correlation coefficient was determined by regression analysis.

Example 2

Range Finding Experiment with Alzet Minipumps to Determine the No-Observable-Adverse-Effect-Level (NOAEL) of VCD and Verify Primordial and Primary Follicle Depletion We will use $B6C3F_1$ mice because they are the most completely characterized mouse strain using multiple injections of VCD. The 160 mg/kg/d dose injected i.p. for 15 d yields the greatest acceleration of follicle depletion via a single injection without adverse effects. We know that if the total VCD dose delivered over 15 d (2400 mg/kg) is injected in a single bolus the mice die within hours. Mice can tolerate more VCD per day if it is metered out over the 24 h time period. Our preliminary data indicates that mice tolerate VCD well when dosed 3 times a day @ 80 mg/kg/d (total 240 mg/kg/d). Three injections a day, per mouse, is labor intense and may be impractical for commercial production.

VCD is a member of the 4-vinylcyclohexene family of chemicals and appears to be the bioactive compound in rats and mice. It is rapidly metabolized into the inactive tetrol and polar products. Thus far, only repeated injection of VCD has been examined for its promotion of follicular depletion. Our goal is to reduce the 15 daily injections to one procedure or injection per mouse. To reach this goal we must first determine whether continuous delivery of VCD will elicit follicular depletion similar to the repeated dosing regimen.

To examine the effect of continuous VCD delivery, Alzet minipumps model 1002 will be implanted subcutaneously (sc.). Although repeated injection of VCD has always been performed via an intraperitoneal route, for ease and less stress to the animal we will implant the minipumps sc. Subcutaneous administration of VCD will be an effective route as we know dermal application of VCD in acetone is active and i.p. injection of VCD in DMSO vehicle achieves the same follicular depletion as i.p. injection of VCD in sesame oil. It is even possible that sc. administration may increase the efficacy of VCD as it will not be rapidly inactivated by its first pass metabolism through the portal system which most likely occurs when injected i.p.

The effective plasma concentration of VCD has not been determined. VCD does not absorb visible or UV light and is too small (140.2 molecular weight) to be tagged with a large molecule such as biotin to follow its disposition. Because VCD is not easily detected, the peak concentration of VCD in blood after its injection has not been determined. Intravenous administration of $^{14}$C-tagged VCD shows its rapid conversion into the inactive tetrol form. VCD's half life is 4.4 minutes and its mean residence time is 4.7 minutes. For our purposes we do not need to achieve a target plasma concentration because our goal is operational, to cause follicle depletion without causing generalized toxicity.

Given the short half life of VCD in blood it may be that continuous delivery via minipump will require less VCD to deplete ovarian follicles. Significant reduction in effective concentration when going from injection to infusion is frequently observed. For instance, continuous administration of endostatin by i.p. minipumps decreased the effective dose by 8-10 fold as well as increasing its efficacy. It cannot be assumed that continuous delivery of VCD will increase its efficacy because this must be specifically determined for each chemical. VCD is inexpensive and readily available from numerous suppliers so minimization of VCD use is not a consideration. Instead, the goal is to reduce the number of injections per mouse to reduce stress to the animals, personnel related expenses and the per diem cost for mice in commercial facilities.

Alzet minipump model 1002 will be used to continuously administer VCD. Osmotic minipumps deliver their contents at a constant μl/hr rate. Therefore, to adjust the dose we will change the amount of VCD loaded into the minipump. The first dose tested will be the closest approximation to the dose administered in the 15 daily injections of 160 mg/kg/d (2400 mg/kg). Using Alzet minipump model 1002 which delivers 0.25 μl/hr, it will take approximately 14 days to deliver 95% of the 100 μl reservoir volume.

For the first pilot experiment there will be 6 cycling female mice (age d40) in each of 4 groups. The groups will be; vehicle control receiving 15 daily injections of 50% DMSO, positive control receiving 15 daily injections of VCD in 50% DMSO @ 160 mg/kg/d, vehicle minipump infusion with 50% DMSO, and minipump infusion with VCD in 50% DMSO. The VCD concentration in the minipump will be adjusted for the weight of each mouse. For instance for a 25 gm mouse the delivery rate will be 0.188 mg/hr for 14 days which will deliver continuously the same total amount of VCD delivered by 15 daily injections received by the positive control group. The minipump reservoir is compatible with 50% DMSO. Although VCD is water soluble, diluting it in DMSO will be a more efficient vehicle to work with when filling the minipumps.

Alzet 1002 minipumps will be placed sc. in mice under anesthesia using procedures described by the manufacturer. Mice will be monitored for 24 h after implantation to watch for normal feeding and behavior. Vehicle and VCD filled minipumps will be implanted the same day as injection groups receive their first dose. All mice will be weighed daily and observed for signs of general toxicity such as wasting, reduced activity and reduced grooming. On d15 after the onset of dosing all mice will be killed by exsanguination under anesthesia. Blood will be collected by cardiac puncture, and plasma separated and stored at −20° C. Ovaries will be collected, trimmed free of fat and fixed in Bouin's solution. Uteri will be collected and weighed to use as a bioassay for whole body levels of estradiol. Adrenals, kidneys, and liver will be removed, weighed, and analyzed for gross stress effects. Liver samples will be collected and prepared for histopathologic examination.

If the continuous delivery of VCD at an equivalent dose of 160 mg/kg/d produces adverse effects, then the experiment will be repeated using half the VCD dose (80 mg/kg/d) which will be achieved by using Alzet minipump model 1002 with half as much VCD concentration loaded into the reservoir. If the 80 mg/kg/d dose also results in adverse effects, we will reduce the dose again by half. This will be done until a dose is found that establishes the NOAEL.

Plasma will be analyzed for the liver enzymes alanine aminotransferase (ALT) and aspartate aminotransferase (AST). If liver function is affected by VCD continuous administration then these activities will be significantly elevated in the VCD minipump group versus the vehicle injection and minipump administration. Increased FSH is measured by radioimmunoassays (RIA: sensitivity=200 pg/ml), and is a good index of reduced 17-beta estradiol production by the ovary. It is unclear that 15 d of VCD exposure will reduce the number of estradiol producing follicles so we will determine if FSH levels are significantly elevated. Follicle counts on sectioned and stained ovaries will be done. Daily VCD injections (160 mg/kg/d) for 15 d will result in a 100% reduction in primordial follicle populations and we anticipate that the same will occur in the VCD minipump group. We expect the DMSO injection and minipump control groups will have the same number of primordial follicles. The goal of this experiment is to determine the NOAEL for continuous VCD administration. This dose will be used in Experiment 3 to compare the relative efficacy of VCD given in repeated injection versus continuously.

Example 3

Using the NOAEL from Example 2 to Define the Kinetics of Follicle Depletion and Increase in Plasma FSH, and Determining if Less VCD is Required when Administered by Continuous Delivery Completion of the Example 2 will provide evidence that continuous delivery of VCD by minipump will not cause general toxicity and accomplish follicle depletion similar to 15 daily VCD injections. The VCD NOAEL will be used to analyze the detailed time course of follicle depletion and increased plasma FSH.

The VCD NOAEL will be used in Alzet minipump model 1002 that delivers the reservoir volume in 14 days. There will be 4 groups of d40 female mice, 6 mice/group, killed at each time point. Groups 1 and 2 will receive 15 daily injections of 50% DMSO vehicle and 50% DMSO with VCD (160 mg/kg, i.p.). Groups 3 and 4 will receive minipumps implanted sc. loaded with 50% DMSO vehicle and 50% DMSO with VCD. Mice will be monitored for 24 h after the implantation to watch for normal feeding and behavior. On the day of minipump implant, the injection control groups will receive the first VCD dose. All mice will be weighed daily and watched for signs of general toxicity such as wasting, reduced activity and reduced grooming. The rate of follicle depletion and FSH increase will be determined by killing mice on day 3, 6, 9, 12, 15 and 30 after the onset of injection and infusion dosing. The mice that will be kept until day 30 will have their minipump implants removed under anesthesia on day 21 as suggested by the manufacturer. Minipumps must be removed because once dosing is complete, irritating concentrated salt solution can leak into surrounding tissue. Animals will be killed and tissues harvested and analyzed as described in Example 2.

As before, plasma ALT and AST activities will be measured to gauge liver toxicity. In this experiment with a 30 day time point we expect that plasma FSH will increase significantly and perhaps sooner in VCD infused mice. Primordial and primary follicle populations will be depleted by day 30 in the VCD treatment groups but the relative rate may differ between injection and infusion groups. A 100% follicle depletion of primordial and primary follicles is a desirable end-point as it predicts total follicle depletion with 45 days. We may observe that continuous VCD delivery accelerates follicle depletion compared to repeated VCD injection. If this is observed we will adjust the NOAEL to a lower concentration as the lowest dose of VCD is desirable.

Example 4

Using the VCD NOAEL from Example 3 and Determining if Time Frame of its Administration can be Less than 14 d Our goal is to reduce mouse per diem cost by shortening the time frame of VCD dosing. We will use the effective VCD dose and administer it in Alzet minipumps that deliver 95% of their reservoir volume in 1 day, 3 days, 7 days and 14 days. Mice can tolerate more VCD when administered in more frequent lower doses (preliminary data FIG. 4). Thus we anticipate that shortening the dosing time frame will be tolerated by the mice making the generation of animal model more economical and feasible for commercial purposes.

There will be 2 groups of d40 female mice, 6 mice/group, that have vehicle or VCD minipumps implanted. In this experiment only minipumps will be used, no injections will be used to administer vehicle/VCD. The VCD NOAEL will be used to fill Alzet minipump models as described below, and deliver 50% DMSO vehicle or VCD in 50% DMSO in 1 day model 2001D=8.0 μl/hr, 3 days model 1003D=1.0 μl/hr, 7 days model 1007D=0.5 μl/hr, and 14 days model 1002=0.25 μl/hr. Mice will be monitored for 24 h after the sc. implantation to watch for normal feeding and behavior. All mice will be weighed daily and watched for signs of general toxicity such as wasting, reduced activity and reduced grooming. All mice will be sacrificed on day 15. Blood will be collected by cardiac puncture, and plasma separated and stored at −20° C. Ovaries will be collected, trimmed free of fat and fixed in Bouin's solution. Tissues will be harvested and analyzed as previously described. Liver samples will be collected and prepared for histopathologic examination.

As before, plasma ALT and AST activities will be measured to gauge liver toxicity. Accelerated VCD delivery may make mice sick and we will carefully monitor them for signs of poor tolerance and perform euthanasia where necessary. Since mice injected 3 times a day with 80 mg/kg/injection tolerated VCD as well as mice injected once a day with 160 mg/kg we expect that the minipump time frame shortened to 7 days will be tolerated by the mice. It is difficult to predict the outcomes for mice receiving the full VCD dose continuously in 1 or 3 days. Mice injected with the full VCD dosed in one bolus died so perhaps infusion in 24 hours will also kill the mice.

Example 5

Capturing the Peri and Post Menopause Endocrine Windows using ½ and ¼ of the Dose Identified in Experiment 3 with the Time Frame Determined from Example 4

To this point we have used VCD dosing that accelerates follicle depletion to achieve complete ovarian failure or partial follicular depletion without causing general toxicity. Reducing VCD dose slows the rate of follicle depletion so that a peri menopause like state can be generated. To our knowledge there is no other mouse model that can simulate the endocrine status of peri-menopause. Our animal model provides the opportunity to study diseases that begin during peri-menopause such as loss of bone mineral density seen in osteoporosis. We anticipate users who want to investigate their diseases in peri-menopausal model mice. To provide this model variation we will define the pharmacokinetics of VCD continuous delivery that protracts the rate of follicle depletion leading to a peri-menopause like endocrine state.

There will be 4 groups of d40 female mice, 6 mice/group, that have vehicle or VCD loaded minipumps implanted. The VCD dosing time frame will define the Alzet minipump model to be used. Group 1 will be implanted with 50% DMSO vehicle, group 2 will receive the dose, group 3 will receive ½ the dose of group 2 and group 4 will receive ¼ the dose of group 2. Mice will be monitored for 24 h after the sc. implantation to watch for normal feeding and behavior. All mice will be weighed daily and watched for signs of general toxicity such as wasting, reduced activity and reduced grooming. Mice will be sacrificed on days 15, 30 and 60. Blood will be collected by cardiac puncture, and plasma separated and stored at −20° C. Tissues will be harvested and analyzed as previously described.

Since we are reducing the VCD NOAEL in this experiment we will not need to monitor liver toxicity so will not measure ALT or AST or perform histopahtologic examination. We will count follicles in ovarian sections and measure FSH in the plasma samples for each time point and VCD dose tested. We anticipate that less VCD will reduce the rate of follicle depletion which will be reflected in higher follicle counts at each time point and FSH will not rise as quickly as observed with the highest dose of VCD. We will compare the rates of follicle depletion for each VCD dose by graphing the % of follicles left with each dose over time to derive the slope of the line that provides the depletion rate.

Accomplishment of this work will demonstrate feasibility of transition from a 15 d i.p. injection protocol to a single-procedure infusion protocol, that results in a peri- and post-menopausal mouse model. Minipumps are too expensive, at >$20/minipump, and require surgical procedures to implant/explant and therefore, may not be feasible for commercial production of the animal model of the present invention. Development of a cost-effective protocol will facilitate commercialization of the model.

General Methods for Examples 2-5

Animals: Female B6C3F, mice will be obtained from JAX (Sacramento, Calif.), housed in plastic cages, and maintained on 12 hour light-dark cycles at 22±2° C. Animals will acclimate to the facilities for 1 week prior to treatment. Food and water will be available ad libitum.

Treatment: Mice will be weighed to determine VCD dose for minipumps and/or injection with VCD (15 d, sc, 160 mg/kg, Sigma-Aldrich, St. Louis, Mo.) or 50% DMSO (vehicle control, n=6/group). Whole blood will be collected by cardiac puncture and plasma separated and stored at −20° C. On kill dates, animals will be weighed, euthanized and the ovaries, uteri, adrenals, kidneys, spleen, and livers collected and weighed.

Histology and Follicle Counting: Ovaries will be trimmed free of fat and placed in Bouin's fixative (2 hours), transferred to 70% ethanol, paraffin-embedded and serially sectioned (4-5 µm), mounted and stained with hematoxylin and eosin. In every $20^{th}$ section, follicles will be classified as previously described.

Assessment of Hepatic Function: Hepatocellular histopathology and enzymatic activity of circulating AST and ALT will be determined by the Diagnostic Laboratory at the Arizona Health Sciences Center.

Hormone Assay: Plasma FSH will be measured by RIA according to instructions from the National Hormone and Pituitary Distribution Program. Samples will be assayed in duplicate. Sensitivity of the assay is 200 pg/ml. Results will be calculated by four-parameter logistic analysis using the software AssayZap (BioSoft, Ferguson, Mo.).

Data Analysis: The effect of VCD treatment on follicle number will be determined by student's t test between two group means for parametric data, and for nonparametric data by Kruskal-Wallis. Tissue weights, liver enzyme levels, and plasma hormone concentrations, will be averaged for each treatment and the means (±SEM) in control versus treated animals will be analyzed for significant differences by one-way analysis of variance (ANOVA). Post-hoc tests (Tukey-Kramer) will be used where appropriate. Tests for homogeneity of variance (Bartlett's) and normality (Shapiro-Wilk) will be routinely performed to assure the assumptions of the ANOVA are met. To determine the no-observed-adverse-effect level (NOAEL), effects of treatment on total body weights, and follicle counts will be analyzed by Student's t-test. The incidence scores of the histopathological data will be analyzed by the Fisher exact test. Significance for all tests will be set at $p<0.05$.

Vertebrate Animals:

1) Female $B6C3F_1$ will be used because the preliminary data has been collected in this strain. All experimental protocols with animals will be conducted at Northern Arizona University under IACUC approved protocols. Litters of 10 female $B6C3F_1$ pups at 21 days of age with a nursing mother will be obtained (Jackson Laboratories, Bar Harbor, Me.). The number of animals used is estimated to be the minimum required to perform these experiments without wasting animals because of inadequate sampling size. NOTE: each animal can serve as a separate n; however, in view of the fact that most animals may be maintained for an extended period of time, animal numbers have been increased by 20% to allow for animal loss. Experiments will be performed on an ongoing basis, and most animals will be maintained for an average of 60 days. Numbers of animals used are indicated in the methods and design for each experiment. Once received, animals will be allowed to acclimate one week prior to the onset of dosing. Animals will be kept in plastic cages (4/cage), maintained on 12-h light/12-h dark cycles (22° C.) and provided food (Purina rat chow) and water ad libitum. On d 40 of age, animals will be dosed daily for 15 days with and sc. injection of vehicle control 50% DMSO, or 4-vinylcyclohexene diepoxide (VCD) or implanted with vehicle or VCD loaded Alzet osmotic minipumps per the manufacturers instructions. At the appropriate time, animals will be killed by pentobarbital overdose (245 mg/kg, i.p.), and blood drawn and tissues removed for histological evaluation.

2) The laboratory mouse is well-defined as a research animal. Preliminary studies to determine the optimal dosing conditions for inducing ovarian failure have been conducted in the $B6C3F_1$ strain. Therefore, the proposed studies will continue with this strain. The number of animals requested has been carefully calculated to provide sufficient amounts of blood and tissue samples for the experiments planned. The numbers calculated have also taken into account appropriate measurements for statistical strength. The experiments proposed do not duplicate previous studies performed by us, or reported by others.

3) All animal care will be provided under the supervision of a board-certified laboratory veterinarian of NAU's PHS approved laboratory animal facility. All procedures will be approved by the Northern Arizona University Institutional Animal Care and Use Committee.

4) All procedures with animals are designed to cause minimal distress or discomfort. Animals will receive daily sc. injections of vehicle (50% DMSO) or test compound (VCD) for 15 days or less. This route of injection has been chosen because previous work has demonstrated reproducible follicle loss is produced. However, follicle loss also occurs with VCD following oral, dermal, or inhalation exposure. Overall, the sc. route of exposure provides minimal trauma to the test animals, requires no sophisticated equipment (such as exposure chambers) and reduces risk of exposure of personnel. Subcutaneous implantation of Alzet osmotic minipumps will be performed under pentobarbital anesthesia and the wound will be closed with clips or sutures. The mice will be closely observed for signs of distress or infection. All personnel involved have been trained to humanely accomplish these tasks.

5) All animals will be euthanized by pentobarbital overdose (245 mg/kg, i.p.). This method is consistent with the recommendations of the Panel on Euthanasia of the American Veterinary Association.

REFERENCES

1. Lobo R, Kelsey J, Marcus R. Menopause: biology and pathobiology. 1 ed. San Diego: Academic Press; 2000.
2. Mosca L, Manson J E, Sutherland S E, Langer R D, Manolio T, Barrett-Connor E. Cardiovascular disease in women: statement for healthcare professionals from the American Heart Association. Circulation 1997; 96:2468-82.
3. Oparil S. Hormones and Vasoprotection. Hypertension 1999; 33(II:170-6.
4. Hulley S, Grady D, Bush T. Randomized trial of estrogen plus progestin for secondary prevention of coronary heart disease in post-menopausal women. Heart and Estrogen/progestin Replacement Study (HERS) Research Group. JAMA 1998; 280:605-13.
5. Writing Group for the Women's Health Initiative Investigators. Risks and benefits of estrogen plus progestin in healthy postmenopausal women. J. Amer. Med. Assoc. 2002; 288:321-333.
6. Purdie D W. Consequences of long-term hormone replacement therapy. Brit. Med. Bull. 2000; 56:809.
7. Rodriguez C, Pantel A V, Calle E E, Jacob E J, Thun M J. Estrogen replacement therapy and ovarian cancer mortality in a large prospective study of US women. J. Amer. Med. Assoc. 2001; 285:1460.
8. Erickson G F. Ovarian anatomy and physiology. In: Lobo R, Kelsey J, Marcus R, editors. Menopause, Biology and Pathobiology. 1 ed. San Diego: Academic Press; 2000. p 13-31.
9. Bellino F L. Nonprimate animal models of menopause: Workshop report. Menopause 2000; 7(1):14-24.
10. Judd H L. Hormonal dynamics associated with the menopause. Clinical Obstetricts and Gynecology 1976; 19(4):775-88.
11. Flaws J A, Doerr J K, Sipes I G, Hoyer P B. Destruction of preantral follicles in adult rats by 4-vinyl-1-cyclohexene diepoxide. Reproductive Toxicology 1994; 8(6):509-14.
12. Kao S-W, Sipes I G, Hoyer P B. Early effects of obotoxicity induced by 4-vinylcyclohexene diepoxide in rats and mice. Reproductive Toxicology 1999; 13(1):67-75.
13. Smith B J, Mattison D. R., Sipes I G. The role of expoxidastion in 4-vinylcyclohexene-induced ovarian toxicity. Toxicology and Applied Pharmacology 1990; 105:372-81.
14. Springer L N, McAsey M E, Flaws J A, Tilly J L, Sipes I. G., Hoyer P B. Involvement of apoptosis in 4-vinylcyclohexene diepoxide induced ovotoxicity in rats. Toxicol Appl Pharmacol August 1996; 139(2):394-401.
15. Mayer L P, Pearsall N A, Christian P J, Devine P J, Payne C M, McCuskey M K, Marion S L, Sipes I. G., Hoyer P B. Long-term effects of ovarian follicular depletion in rats by 4-vinylcyclohexene diepoxide. Reproductive Toxicology 2002;In press.
16. Devine P J, Payne C M, McCuskey M K, Hoyer P B. Ultrastructural evaluation of ooxyted during atresia in rat ovarian follicles. Biol. Reprod. 2000; 63:1245-1252.
17. Hu X, Christian P J, Sipes I. G., Hoyer P B. Expression and redistribution of cellular Bad, Bax, and Bcl-X(L) protein is associated with VCD-induced ovotoxicity in rats. Biology of Reproduction 2001 November; 65(5):1489-95.
18. Hu X, Christian P J, Thompson K E, Sipes I G, Hoyer P B. Apoptosis induced in rats by 4-vinylcyclohexene diepoxide is associated with activation of the caspase cascades. Biology of Reproduction 2001; 65(1):87-93.
19. Hu X, Flaws J A, Sipes I. G., Hoyer P B. Activation of Mitogen-Activated Protein Kinases and AP-1 Transcription Factor in Ovotoxicity Induced by 4-vinylcyclohexene Diepoxide in Rats. Biology of Reproduction 2002;In press.
20. Borman S M, VanDePol B J, Kao A, Thompson K E, Sipes I G, Hoyer P B. A single dose of the ovotoxicant 4-vinylcyclohexene diepoxide is protective in rat primary ovarian follicles. Toxicology and Applied Pharmacology 1999; 158:244-52.
21. Thompson K E, Sipes I. G., Greenstein B D, Hoyer P B. 17-estradiol affords protection against 4-vinylcyclohexene diepoxide-induced ovarian follicle loss in Fisher-344 rats. Endocrinology 2002; 143 (3):1058-65.
22. Hooser S B, Douds D P, DeMerell D G, Hoyer P B, Sipes I G. Long-term ovarian and gonadotropin changes in mice exposed to 4-vinylcyclohexene. Reproductive Toxicology 1994; 8(4):315-23.

Obviously, numerous modifications and variations of the present invention are possible in light of the above teachings. It is therefore to be understood that within the scope of the appended claims, the invention may be practiced otherwise than as specifically described herein.

The invention claimed is:

1. A mammalian non-human female animal having a complete depletion of ovarian primordial follicles and at least one characteristic selected from the group consisting of depletion of ovarian follicles, irregular ovarian cyclicity, cessation of estrous cyclicity, elevated FSH levels, erratic ovarian 17β-estradiol levels, loss of bone mineral density, and reduced ovarian weight, wherein the animal has been administered 4-vinylcyclohexene diepoxide at a dosage of 100 mg/kg/day to 720 mg/kg/day.

2. The animal of claim 1, wherein the animal has been administered 4-vinylcyclohexene diepoxide at a dosage of 100 mg/kg/day to 200 mg/kg/day for at least 10 days.

3. The animal of claim 1, which is suitable as a model of menopause.

4. The animal of claim 1, which is suitable as a model of perimenopause.

5. The animal of claim 1, which has irregular ovarian cyclicity.

6. The animal of claim 1, which has cessation of estrous cyclicity.

7. The animal of claim 1, which has elevated FSH levels.

8. The animal of claim 1, which has erratic ovarian 17β-estradiol levels.

9. The animal of claim 1, which has loss of bone mineral density.

10. The animal of claim 1, which has reduced ovarian weight.

11. The animal of claim 1, which is a mouse.

12. The animal of claim 1, which is a rat.

13. The animal of claim 1, which is a primate.

14. The animal of claim 1, which is a canine.

15. A method of preparing the animal of claim 1, comprising administering to the animal 4-vinylcyclohexene diepoxide at a dosage of 100 mg/kg/day to 700 mg/kg/day, to produce a complete depletion of ovarian primordial follicles and at least one characteristic selected from the group consisting of depletion of ovarian follicles, irregular ovarian cyclicity, cessation of estrous cyclicity, elevated FSH levels, erratic ovarian 17β-estradiol levels, loss of bone mineral density, and reduced ovarian weight.

16. The method of claim 15, wherein the 4-vinylcyclohexene diepoxide is administered intraperitoneally (i.p.), subcutaneously (s.c.), or by an implantable device.

17. The method of claim 15 wherein the 4-vinylcyclohexene diepoxide is administered to the animal for at least 10 days.

18. A method of inducing ovarian failure in a mammalian non-human female animal other than a mouse or a rat, comprising administering to the animal 4-vinylcyclohexene diepoxide at a dosage of 100 mg/kg/day to 720 mg/kg/day, to cause ovarian failure in the animal.

19. The method of claim 18, wherein the animal is a canine.

20. The method of claim 18, wherein the animal has been administered 4-vinylcyclohexene diepoxide at a dosage of 100 mg/kg/day to 250 mg/kg/day.

21. The method of claim 18, wherein the animal has been administered 4-vinylcyclohexene diepoxide at a dosage of 100 mg/kg/day to 250 mg/kg/day for at least 10 days.

22. The method of claim 18, wherein the animal is selected from the group consisting of cats, hamsters, ferrets, rabbits, sheep, cattle, horses, pigs, deer, elk, moose, bears, goats, monkeys, and wild felines.

23. A method of controlling the size of a mammalian non-human animal population, comprising administering 4-vinylcyclohexene diepoxide at a dosage of 100 mg/kg/day to 720 mg/kg/day, to cause at least partial ovarian failure in at least a portion of the female members of the animal population and control the size of the population.

24. The method of claim 23, wherein the animal is selected from the group consisting of dogs, cats, hamsters, ferrets, rabbits, sheep, cattle, horses, pigs, deer, elk, moose, bears, goats, monkeys, and wild felines.

25. The method of claim 23, wherein the animal has been administered 4-vinylcyclohexene diepoxide at a dosage of 100 mg/kg/day to 250 mg/kg/day.

26. The method of claim 23, wherein the animal has been administered 4-vinylcyclohexene diepoxide at a dosage of 100 mg/kg/day to 250 mg/kg/day for at least 10 days.

27. The method of claim 1, wherein the VCD is administered at a dosage of 100 mg/kg/day to 500 mg/kg/day.

28. The method of claim 1, wherein the VCD is administered at a dosage of 100 mg/kg/day to 250 mg/kg/day.

29. The method of claim 1, wherein the VCD is administered at a dosage of 100 mg/kg/day to 160 mg/kg/day.

30. The method of claim 18, wherein the VCD is administered at a dosage of 100 mg/kg/day to 500 mg/kg/day.

31. The method of claim 18, wherein the VCD is administered at a dosage of 100 mg/kg/day to 250 mg/kg/day.

32. The method of claim 18, wherein the VCD is administered at a dosage of 100 mg/kg/day to 160 mg/kg/day.

33. The method of claim 23, wherein the VCD is administered at a dosage of 100 mg/kg/day to 500 mg/kg/day.

34. The method of claim 23, wherein the VCD is administered at a dosage of 100 mg/kg/day to 250 mg/kg/day.

35. The method of claim 23, wherein the VCD is administered at a dosage of 100 mg/kg/day to 160 mg/kg/day.

36. The animal of claim 1, wherein the animal is a mouse which has been administered 4-vinylcyclohexene diepoxide at a dosage of 160 mg/kg/day to 720 mg/kg/day for at least 15 days.

* * * * *